(12) United States Patent
Hartman et al.

(10) Patent No.: US 9,364,551 B2
(45) Date of Patent: Jun. 14, 2016

(54) LIGHT-ENABLED DRUG DELIVERY

(71) Applicant: Virginia Commonwealth University, Richmond, VA (US)

(72) Inventors: Matthew Hartman, Richmond, VA (US); Martin Michael Dcona, Richmond, VA (US); Deboleena Mitra, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/347,656

(22) PCT Filed: Sep. 28, 2012

(86) PCT No.: PCT/US2012/057846
§ 371 (c)(1),
(2) Date: Mar. 27, 2014

(87) PCT Pub. No.: WO2013/049521
PCT Pub. Date: Apr. 4, 2013

(65) Prior Publication Data
US 2014/0236071 A1     Aug. 21, 2014

Related U.S. Application Data

(60) Provisional application No. 61/540,581, filed on Sep. 29, 2011.

(51) Int. Cl.
| | |
|---|---|
| A61K 38/00 | (2006.01) |
| C07K 2/00 | (2006.01) |
| A61K 47/48 | (2006.01) |
| A61K 41/00 | (2006.01) |
| A61K 31/704 | (2006.01) |
| A61N 5/06 | (2006.01) |

(52) U.S. Cl.
CPC ......... *A61K 47/48023* (2013.01); *A61K 31/704* (2013.01); *A61K 41/0042* (2013.01); *A61K 47/48238* (2013.01); *A61K 47/48338* (2013.01); *A61N 5/062* (2013.01)

(58) Field of Classification Search
None
See application file for complete search history.

(56) References Cited

U.S. PATENT DOCUMENTS

| | | |
|---|---|---|
| 2005/0169933 A1 | 8/2005 | Steeves et al. |
| 2010/0092495 A1 | 4/2010 | Chari |

OTHER PUBLICATIONS

Shamay et al, Light induced drug delivery into cancer cells (Biomaterials 32 (2011) 1377-1386).*
Law et al, A mitochondrial targeted fusion peptide exhibits remarkable cytotoxicity (Mol Cancer Ther 2006;5(8). Aug. 2006).*
Constance et al, Targeting malignant mitochondria with therapeutic peptides (Ther Deliv. Aug. 2012 ; 3(8): 961-979).*
Madani et al, Mechanisms of Cellular Uptake of Cell-Penetrating Peptides (Journal of Biophysics, vol. 2011, Article ID 414729).*
Shamay et al., "Light induced drug delivery into cancer cells", Biomaterials, Nov. 12, 2010, pp. 1377-1386, vol. 32, No. 5.
Choi et al., "Light-controlled release of caged doxorubicin from folate receptor-targeting PAMAM dndrimer nanoconjugate", Chem Comm, 2010, pp. 2632-2634, vol. 46, No. 15.
Alvarez-Lorenzo et al., "Light-sensitive intelligent drug delivery systems", Photochemistry and Photobiology, 2009, pp. 848-860, vol. 85, No. 4.

* cited by examiner

*Primary Examiner* — Marcela M Cordero Garcia
*Assistant Examiner* — Sergio Coffa
(74) *Attorney, Agent, or Firm* — Whitham, Curtis & Cook, P.C.

(57) ABSTRACT

Conjugates are provided which comprise a membrane permeable drug linked to a moiety that is not membrane permeable. Attachment of the moiety that is not membrane permeable prevents the drug from crossing cell membranes and entering cells. However, exposure to light either i) breaks the linkage, releasing the drug and allowing it to enter cells; or ii) converts the non-membrane permeable moiety to a membrane permeable form, allowing the entire conjugate to enter the cell, where the drug is released from the conjugate by cleavage. The membrane permeable drugs are thus delivered to cells at locations of interest, e.g. cancer cells in a tumor, in a temporally and spatially controlled manner.

10 Claims, 16 Drawing Sheets

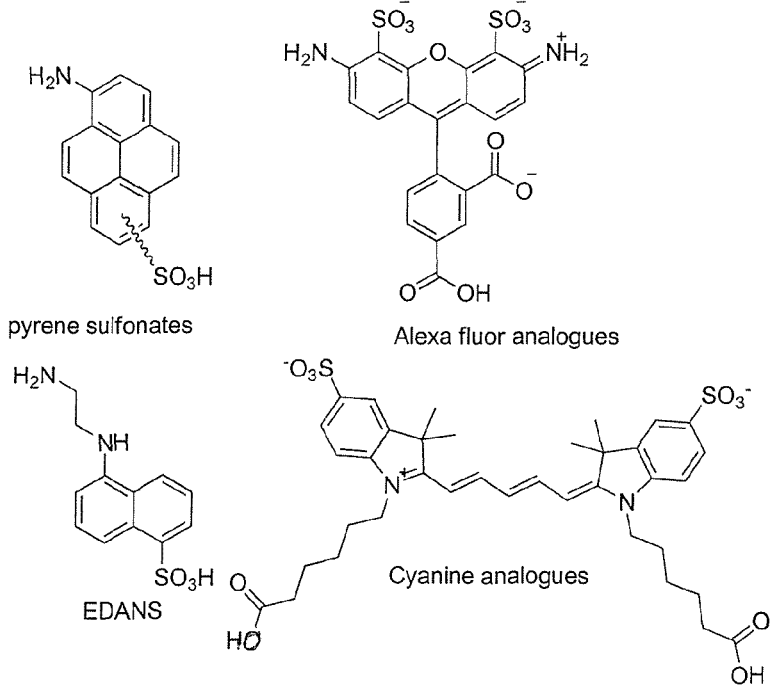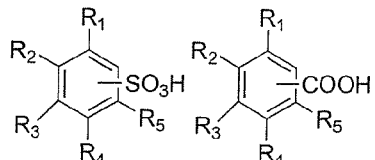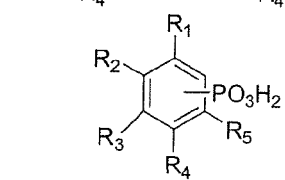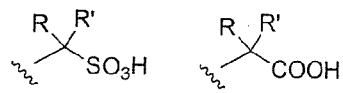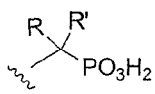
Figure 2 A and B

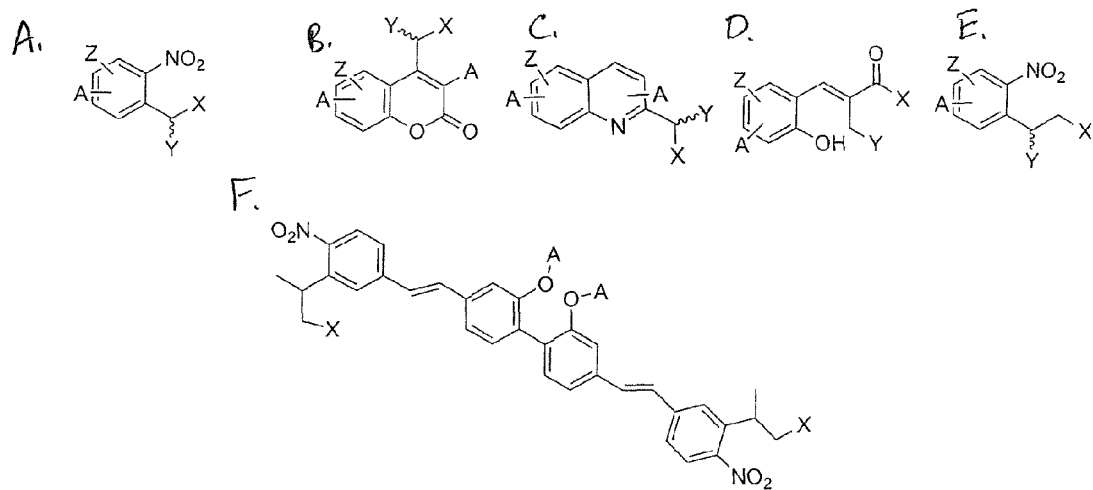
A = site of attachment for hydrophilic linker
X = N,O,S, carbamate, carbonate (site of drug attachment)
Y = C-R, O-R, N-R, H
Z = H, OR (1 or multiple), halogen
additional aromatic rings
Figure 3 A-F

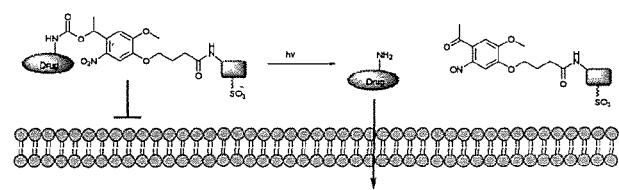
Figure 4
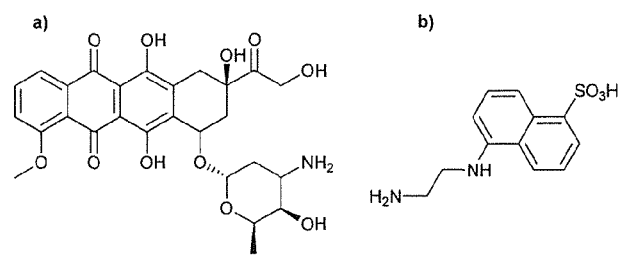
Figure 5A and B

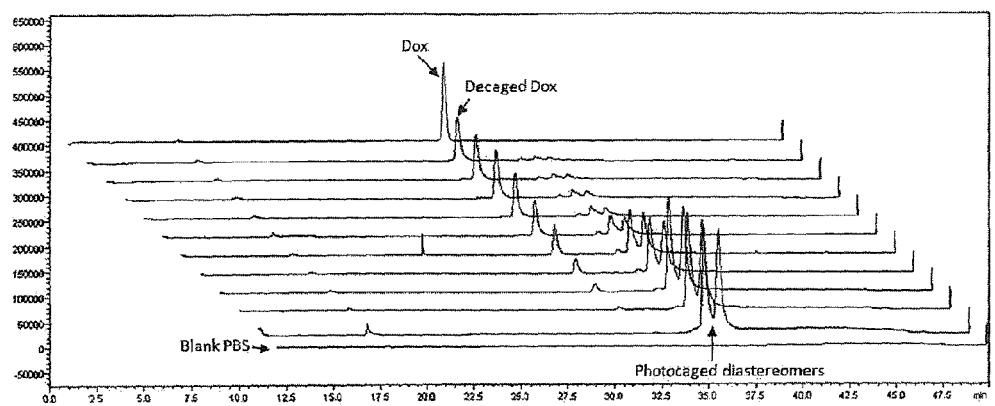
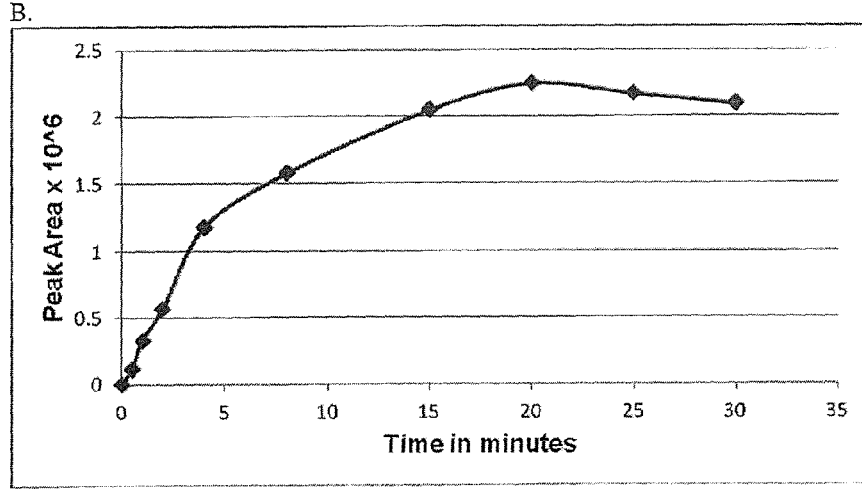
Figure 6A and B.

A.
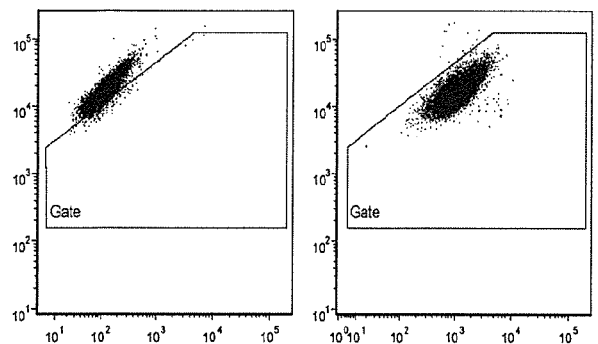
B.
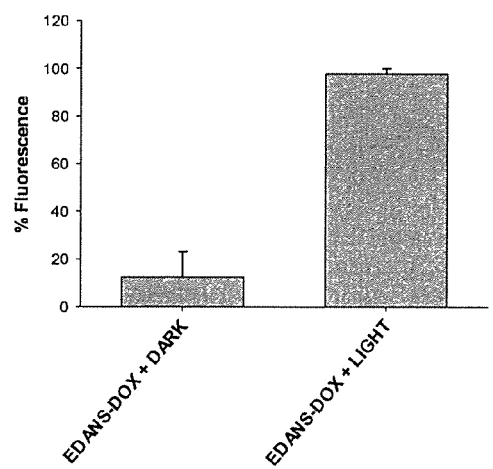
Figure 7A and B

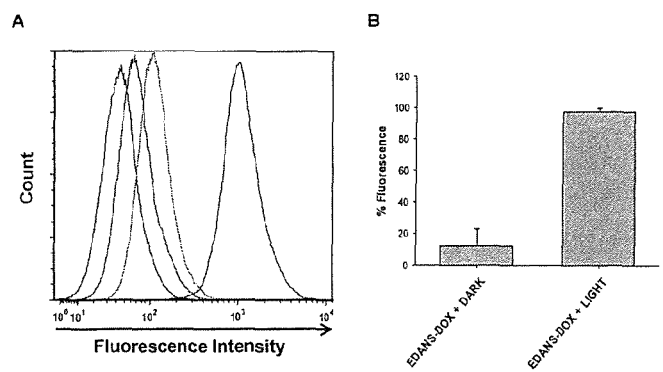
Figure 8 A and B

\*-EACARVXAACEAAARQ Woolley SEQ ID NO: 1
\*-<u>R</u>ACARVXAAC<u>R</u>AAARQ Peptide 1 SEQ ID NO: 2
\*-EAAAREACARECAARQ Woolley SEQ ID NO: 3
\*-<u>R</u>AAAREACAR<u>R</u>CAARQ Peptide 2 SEQ ID NO: 4

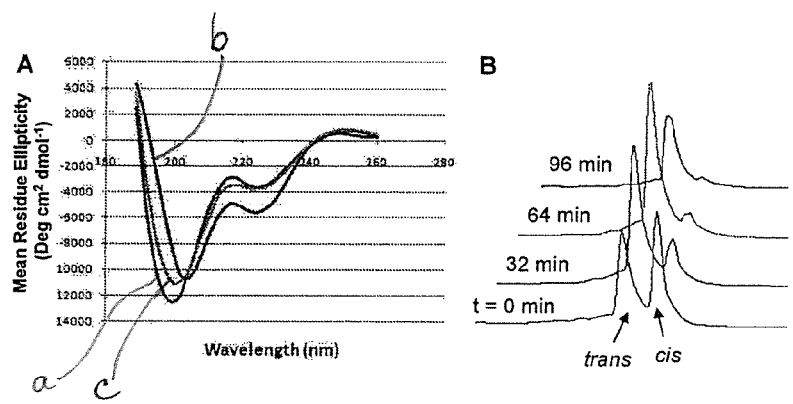
Figure 19A and B

SEQUENCE LISTING

<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X = 2-aminoisobutyric acid

<400> SEQUENCE: 1

```
Glu Ala Cys Ala Arg Val Xaa Ala Ala Cys Glu Ala Ala Ala Arg Gln
1               5                   10                  15
```

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X = 2-aminoisobutyric acid

<400> SEQUENCE: 2

```
Arg Ala Cys Ala Arg Val Xaa Ala Ala Cys Arg Ala Ala Ala Arg Gln
1               5                   10                  15
```

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

```
Glu Ala Ala Ala Arg Glu Ala Cys Ala Arg Glu Cys Ala Ala Arg Gln
1               5                   10                  15
```

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

```
Arg Ala Ala Ala Arg Glu Ala Cys Ala Arg Arg Cys Ala Ala Arg Gln
1               5                   10                  15
```

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X = 2-aminoisobutyric acid

<400> SEQUENCE: 5

```
Cys Arg Ala Cys Ala Arg Val Xaa Ala Ala Cys Arg Ala Ala Ala Arg
1               5                   10                  15

Gln
```

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

```
Cys Arg Ala Ala Ala Arg Glu Ala Cys Ala Arg Arg Cys Ala Ala Arg
1               5                   10                  15

Gln
```

```
<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X = 2-aminoisobutyric acid

<400> SEQUENCE: 7

Arg Ala Cys Ala Arg Val Xaa Ala Ala Cys Arg Ala Ala Ala Arg Gln
1               5                   10                  15
```

LIGHT-ENABLED DRUG DELIVERY

BACKGROUND OF THE INVENTION

1. Field of the Invention

The invention generally relates to novel compositions and methods for targeted delivery of a membrane permeable drug to cells by temporarily rendering it membrane impermeable. In particular, the invention provides conjugates comprising a membrane permeable drug linked to a moiety that is not membrane permeable, thereby preventing the drug from entering cells. Light exposure either i) cleaves the linkage, allowing the drug to enter the cells or ii) allows the conjugate to enter the cell, wherein the linkage is cleaved and the drug is released.

2. Background of the Invention

A major challenge of drug delivery is insuring bioavailability. Usually, drugs must be water soluble, and hence hydrophilic, in order to be successfully administered in vivo. At the same time, in order to reach a targeted location of action, the drug must usually enter and/or cross biological membranes, which requires the drug to have hydrophobic properties. Balancing these two opposing requirements is a major challenge when designing drug delivery methods.

A further challenge in drug delivery is the achievement of controlled, targeted delivery. Many drugs are administered systemically in a form that does not allow medical professionals to control when or where the drug will be active. As a result, unwanted, toxic side effects can occur. For example, drugs used for cancer treatment non-selectively attack rapidly dividing cells of all types, not just cancer cells, and usually cause severe side effects in recipients.

There is a need in the art to develop new compositions and methods for controlled, targeted delivery of drugs.

SUMMARY OF THE INVENTION

The invention provides novel compositions and methods for the controlled, targeted, and selective delivery of drugs to a targeted location within the body based on manipulation of membrane permeability of a complex containing a drug of interest. In addition, the methodology described herein is advantageously oxygen independent. According to the invention, the ability of membrane permeable drugs to enter and cross the cell membrane is abolished or attenuated by chemically attaching to them a moiety that is membrane impermeable, thereby forming a conjugate that is also not membrane permeable, but which is advantageous for in vivo administration. In one embodiment, the chemical linkage that is used for the attachment is light sensitive, i.e. exposure to light causes cleavage of the membrane impermeable moiety from the conjugate, releasing the drug. Since the trigger that causes cleavage of the linkage is exposure to light, and since the timing, location and intensity of light exposure can be controlled, this methodology makes it possible to control the timing, location and rate of delivery of the drug to cells with specificity.

In another embodiment, the moiety that is membrane impermeable is a peptide that, upon exposure to light, switches from a membrane impermeable conformation to a membrane permeable conformation. When such a peptide is conjugated to a membrane permeable drug of interest, in the dark, the conjugate of drug and peptide moiety are not membrane permeable. Exposure to light renders the peptide, and hence the conjugate, membrane permeable and the entire conjugate is able to cross the cell membrane. However, conjugates that are not exposed to light, or which are exposed to light but carried away from the membrane and back into darkness before having an opportunity to enter a cell, are switched back to a membrane impermeable state. The drug of interest in such reversible peptide conjugates may be active while still attached to the peptide. Alternatively, the peptide may be cleaved, e.g. by intracellular proteases, releasing the drug in an active form.

It is an object of this invention to provide a conjugate for delivering a membrane permeable drug into cells. The conjugate comprises the membrane permeable drug, and a membrane impermeable moiety chemically attached to said membrane permeable drug. In some embodiments, the membrane impermeable moiety is chemically attached to the membrane permeable drug via a photolabile linkage. In other embodiments, the membrane impermeable moiety comprises a peptide that adopts an α-helical conformation and becomes membrane permeable upon exposure to light. In some embodiments of the invention, the membrane permeable drug is doxorubicin.

The invention also provides methods of providing a membrane permeable drug to cells at a targeted location in a patient in need thereof, comprising I) administering to said patient a conjugate, comprising the membrane permeable drug, and a membrane impermeable moiety chemically attached to the membrane permeable drug, and II) exposing the targeted location to light when the conjugate is at the targeted location. In such embodiments, either i) the membrane impermeable moiety is chemically attached to the membrane permeable drug via a photolabile linkage, and the step of exposing causes cleavage of the photolabile linkage; or ii) the membrane impermeable moiety comprises a peptide that adopts an α-helical conformation and becomes membrane permeable upon exposure to light, and the step of exposing causes the peptide to adopt an α-helical conformation and become membrane permeable. In some embodiments, membrane permeable drug is doxorubicin.

The invention further provides methods of treating a patient having a disease or condition that is treatable by administration of a membrane permeable drug. The methods comprise the steps of i) administering to the patient a conjugate comprising the membrane permeable drug and a membrane impermeable moiety chemically attached to the membrane permeable drug; and ii) exposing a section of the body of the patient that is affected by the disease or condition to light. In further embodiments, the membrane impermeable moiety is chemically attached to the membrane permeable drug via a photolabile linkage, and the step of exposing causes cleavage of the photolabile linkage. In yet other embodiments, the membrane impermeable moiety comprises a peptide that adopts an α-helical conformation and becomes membrane permeable upon exposure to light, and the step of exposing causes the peptide to adopt an α-helical conformation and become membrane permeable. In some embodiments, membrane permeable drug is doxorubicin.

BRIEF DESCRIPTION OF THE DRAWINGS

FIGS. 2A and B. Exemplary hydrophilic molecules. A, chemical formulas of: an exemplary pyrene sulfonate, an exemplary Alexa Fluor analogue, 5-((2-aminoethyl)amino) naphthalene-1-sulfonic acid (EDANS), and an exemplary cyanine analog; B, generic chemical formulas of aryl and alkyl sulfonates, phosphonates, phosphates and carboxylic acids, where R=saturated or unsaturated alkyl chains, which may be the same of different in a given molecule, and which contain from 1 to 20 carbon atoms.

FIG. 3A-G. Exemplary photocleavable linkers. A, o-nitrobenzyl; B, Coumarin; C, quinoline; D, o-hydroxycinnamate; E, o-nitrophenethyl; F, biphenyl-donor-acceptor; G, cobalamin.

FIG. 4. Exemplary photocaged permeability strategy for drug delivery.

FIGS. 5A and B. A, the anticancer drug doxorubicin; B, cell impermeable EDANS.

FIGS. 6A and B. A, Release of free dox with upon irradiation over time. A solution of Dox EDANS (compound 9) was irradiated. Samples were removed at various time points (0.5, 1, 2, 4, 8, 15, 20, and 30 min) and were analyzed by RP-HPLC at λ=480 nm. The compound in the dark (t=0) and free doxorubicin are included as standards. B, Graph representing increase in intensity of integrated peak area of doxorubicin in the above time dependent photolysis experiment.

FIGS. 7A and B. Flow cytometry analysis of EDANS-Dox with JH-EsoAd1 cells in the dark and upon illumination (9.0 mW/cm2) for 20 min. A, Representative dot plot of the relative fluorescence intensity of EDANS-DOX in Light or Dark. The gate shown was used to derive the % Fluorescence data shown in the right panel. B, Quantification of DOX fluorescence for the indicated treatment conditions. Data are representative of two independent experiments, N=9.

FIGS. 8A and B. A, The flow cytometry histogram displays the relative fluorescence intensity of untreated controls in the dark or light or JH-EsoAd1 cells treated with EDANS-Dox in the dark or light. B, Quantification of Dox fluorescence for the indicated treatment conditions. Data are representative of two independent experiments, N=9.

FIGS. 19A and B. Evidence for Photoswitching. A, CD studies at 25° C. showing a, dark adapted, b, illumination for 5 min, and c, 30 minutes after removal of light; B, HPLC chromatograms of Peptide 1 at various times post-irradiation showing thermal relaxation from the cis to back to the trans ground state. Peaks were detected at 310 nm, an isosbestic point for the two forms.

DETAILED DESCRIPTION

Figure 1:
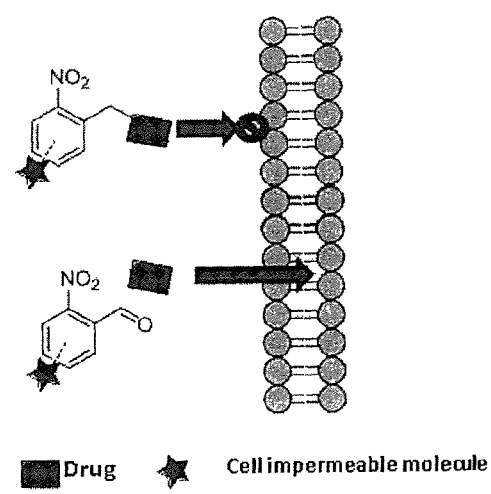
FIG. 1. Schematic representation of a prodrug of the invention with a cell permeable drug (represented by a rectangle) that is unable to enter the cell because it is attached to a cell impermeable molecule (represented by a star) via a photolabile linkage. The drug is released upon cleavage of the linkage by light.
Figure 3G:
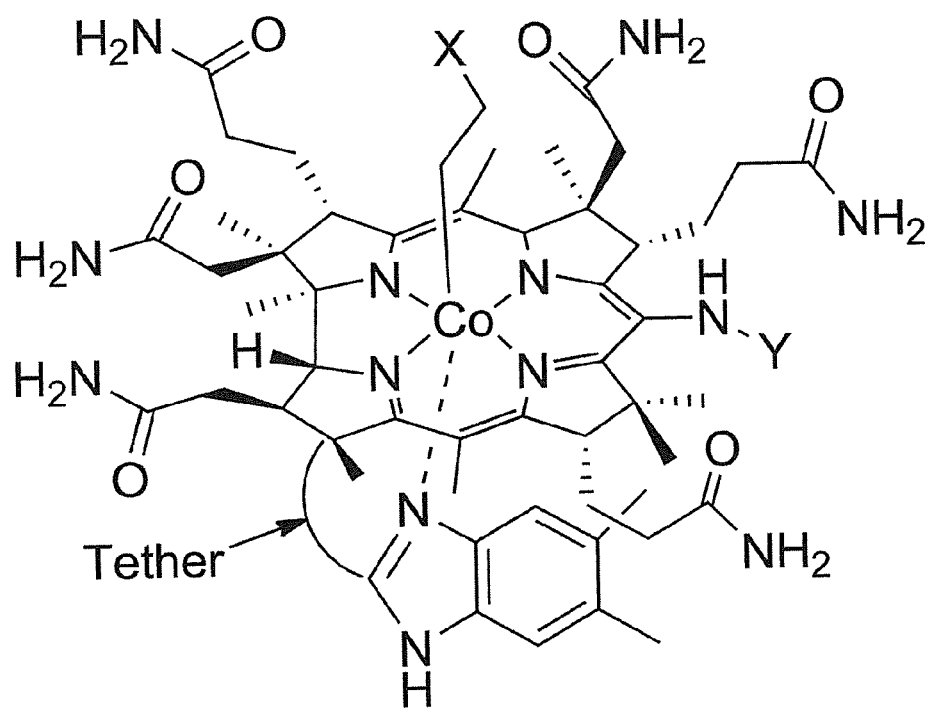

Selectivity and control of pharmacological action is of central importance in drug therapy. Conjugates that provide such selectivity and control, and methods of using the same, are provided by the invention. This is accomplished via manipulation of membrane permeability of the drug.

In one embodiment, the cell permeable drug of interest is modified by attachment of a cell impermeable group via a light-scissile linker. In the dark, the cell impermeable group prevents the drug from reaching its intracellular target(s). Upon irradiation, the drug is released, allowing its entry into the cell. This method allows drugs to be targeted to cells with spatiotemporal control. Drug conjugates of this type may be referred to herein as photocaged.

In a second embodiment, the moiety that is membrane impermeable is a peptide. However, this embodiment differs from that described above in that exposure to light does not cause cleavage of the bond between the peptide and the membrane permeable drug of interest. Instead, exposure to light causes a change in the conformation of the peptide, and renders it membrane permeable. Therefore, the entire conjugate (drug plus peptide) is able to cross the cell membrane and enter the cell. Once inside the cell, the drug of interest may be released from the conjugate via proteolytic cleavage or degradation of all or a portion of the peptide. Alternatively, in some embodiments, the drug is active while attached to the peptide. This embodiment is advantageous in that the peptide is photoswitchable and may be converted back and forth from a membrane impermeable state (in the dark) to a membrane permeable state (in the light), and then back again to a membrane impermeable state once light is removed, or once the conjugate is out of range of the light source. Thus, in contrast to the photocaged conjugates described above, the membrane permeability of the peptide conjugates is reversible so that, if diffusion or blood flow carries a light-activated membrane permeable complex from its intended site of activation, permeability is "switched off" upon egress from the intended region of action. Drug conjugates of this type may be referred to herein as reversible or switchable peptide conjugates.

DEFINITIONS

A "drug" (which may be referred to herein as an "active agent") refers to a compound that has biological activity, usually a biological activity that provides a beneficial effect to a recipient, e.g. to cure, prevent or ameliorate disease symptoms, or symptoms of an undesirable medical condition.

A "prodrug" is a drug or active agent that is typically delivered as part of a larger inactive molecule or conjugate (complex) (e.g. conjugated or chemically attached to one or more other non-drug molecules or moieties), the drug or active agent being released in an active form after administration.

"Membrane permeable" drugs are drugs which can traverse the cell bilayer and enter cells. Generally, membrane permeable drugs are small hydrophobic and/or lipophilic, and the terms "membrane permeable" and "hydrophobic" may be used interchangeably herein. Membrane permeable drugs typically follow Lipinski's "rule of 5, which states that, in general, an orally active drug has no more than one violation of the following criteria:
1) Not more than 5 hydrogen bond donors (nitrogen or oxygen atoms with one or more hydrogen atoms)
2) Not more than 10 hydrogen bond acceptors (nitrogen or oxygen atoms)
3) A molecular mass less than 500 daltons
4) An octanol-water partition coefficient log P not greater than 5 (see, for example, Leo A, Hansch C, and Elkins D (1971). "Partition coefficients and their uses". Chem Rev 71 (6): 525-616, for a discussion of log P). However, some drugs do not conform to this rule and such exceptions are also encompassed by the invention.

By "hydrophobic" we mean compounds having little or no affinity for water. Hydrophobic molecules are generally non-polar molecules that have relatively few hydrogen bond donors or acceptors. Such compounds may also be lipophilic, having a tendency to dissolve in fats, oils, lipids, and non-polar solvents such as hexane or toluene, although this is not always the case. Degrees of hydrophobicity and/or lipophilicity may be determined by methods known in the art, for example, by using the chromatographic hydrophobicity index (CHI) which is based on a rapid gradient HPLC method; various partitioning methods such as determinations of Log P, Log D, etc. Drugs suitable for use in the present invention typically have log P values from −0.4 and 5.6 and a molecular weight of less than 550.

"Membrane impermeable" moieties or agents are moieties that cannot freely traverse the cell bilayer and thus cannot enter cells. A wide variety of membrane impermeable molecules and/or moieties may be conjugated to the membrane permeable drug via a photolabile linkage as described herein. In some embodiments, the moiety that is conjugated is not membrane permeable by virtue of being hydrophilic. By "hydrophilic" we mean that the molecule/moiety is a molecule or molecular entity that is attracted to, and tends to be dissolved by, water. Hydrophilic molecules are generally polar and/or ionic molecules (e.g. as indicated by Log p Log d values) that can accept or donate hydrogen bonds to water. They may contain one or more polar or negatively or positively charged functional groups. Preferably, the hydrophilic molecules utilized in the practice of the invention are non-toxic or minimally toxic, although on balance, some toxicity may be tolerated in order to achieve the increased benefit of focused delivery of the drug to a particular location, and the consequent lack of side effects of drug activity at undesirable locations or in non-targeted cells.

Photolabile or photo-cleavable refers to a chemical bond that is broken, dissociated, etc. by the absorption of light, usually light in the visible or ultraviolet region.

"Photocage" refers to the portion of the molecule containing a light-scissile bond that is removed from the drug upon illumination.

"Reversible ("switchable") peptide" conjugate refers to conjugates which comprise at least one drug of interest chemically bonded to a peptide that is membrane impermeable in the absence of light, but which is switched to a membrane permeable form upon exposure to light. The bond between the drug of interest and the peptide is generally not necessarily light-scissile but is stable in the presence of light, but may be susceptible to specific or non-specific proteolytic cleavage.

I. Photocaged Embodiment

Three components are incorporated into the photocaged prodrugs of the invention: 1) a hydrophobic drug of interest that is membrane permeable; 2) a moiety that alters (decreases or abolishes) the membrane permeability of the drug of interest when conjugated thereto; and 3) a linker joining the drug and the moiety, the linker being photosensitive and susceptible to cleavage when exposed to light (also referred to as a "photocage"). In some embodiments, the drug of interest is a hydrophobic drug that is membrane permeable and the moiety that alters the membrane permeability of the drug is a hydrophilic moiety. Attachment of the hydrophilic moiety to the hydrophobic drug increases the water solubility of the drug and prevents (or decreases) the propensity of the drug to cross cell membranes. As a result, after administration, the drug is distributed largely outside cells until the photolabile linkage between the drug and hydrophobic moiety is broken by exposure to light, which releases the drug to enter and cross cell membranes. Because the application of light can be controlled, e.g. the location of the light source can be controlled so as to emit light over a defined area of interest, the drug is released only at the area of interest. Thus, the area of activity of the drug is circumscribed or largely contained within the targeted area (e.g. at or in the vicinity of a tumor), and entry into non-targeted cells is avoided, or at least curtailed. Unwanted side effects are eliminated, or lessened, in this manner. The invention comprises prodrug conjugates that are linked in this manner, methods of using the prodrugs, and methods of manufacturing the prodrugs.

One embodiment of the invention is illustrated schematically in FIG. 1, which shows a cell impermeable molecule attached to a hydrophobic drug via a photo-labile linkage. As can be seen, when the cell impermeable molecule is chemically bonded to the drug by the light labile linker, entry of the drug into the cell is prevented. However, once the linkage is broken, the drug is freed and can enter the cell. The prodrugs of the invention are designed so that cleavage of the linkage releases the drug intact, or substantially intact, in a form that is active, i.e. the released drug is capable of exerting the desired biological effect. In other words, the drug is released cleanly from the prodrug, with few or no atoms or portions of the prodrug remaining attached to the drug. The linking portion of the prodrug and the membrane impermeable moiety may or may not remain intact upon release of the drug from the conjugate, and the linking portion of the prodrug and the membrane impermeable moiety may or may not remain attached after release of the drug.

Prodrug Components in Photocage Embodiment

Suitable hydrophobic drugs for prodrug formation include but are not limited to:
i) cancer drugs such as doxorubicin, epirubicin; vinca alkaloids; 5-fluororacil; taxol; auristatins; maytansine, mertansine and derivatives thereof; tubulysins; camptothecin; didemnins; cisplatin; methotrexate; calecheamycin; and analogs and derivatives of the above;
ii) Acne vulgaris drugs such as isotretinoin, doxycycline and other tetracycline antiobiotics, trimethoprim, sulfamethoxazole, azithromycin
iii) Psoriasis drugs such as Vitamin A derivatives (like tazarotene), methotrexate, cyclosporin, hydroxyurea, thioguanine, corticosteroids
iv) Actinic keratosis drugs such as 5-fluoro uracil and imiquimod
v) Atherosclerosis drugs; etc.

Any drug that is capable of traversing the cell bilayer and which is attachable to a linking compound as described herein, may be used in the practice of the invention. In some embodiments, this advantageously includes, e.g. for cancer therapy, any molecule with high cytotoxicity, including those not currently being investigated for standard cancer therapy due to their high toxicity, since the present invention protects against the entry of the active, toxic forms into the cell, except under controlled conditions.

Examples of membrane impermeable, and usually hydrophilic, molecules/moieties that may be used in the practice of the invention include but are not limited to: various fluorescent sulfonated molecules such as 5-((2-aminoethyl)amino) naphthalene-1-sulfonic acid (EDANS), pyrene sulfonates, Alexa Fluor analogs (e.g. Alexa Fluor 350, 405, 530, 488, 500, 514, 532, 546, 555, 568, 594, 610, 633, 647, 660, 680, 700, 750, etc.), cyanine analogs belonging to the polymethine group; various aryl or alkyl sulfonates, phosphates, phosphonates and carboxylic acids as known in the art; various highly hydrophilic charged or uncharged molecules such as carbohydrates (e.g. monosaccharides, uronic acids, disaccharides or larger carbohydrate units or derivatives thereof); various membrane impermeable hydrophilic polymers as known in the art; hydrophilic nanoparticles such as, and especially upconverting nanoparticles such as upconverting luminescent nanoparticles; as well as scintillating nanoparticles of various types that convert gamma or X-rays into ultraviolet or visible light; etc. Those of skill in the art will recognize that, with respect to large particles like nanoparticles, the size of the nanoparticle itself is the more important factor in determining cellular permeability rather than its hydrophilic or hydrophobic nature. Exemplary hydrophilic molecules are depicted in FIG. 2.

A wide variety of photolabile (photocleavable, photosensitive, photoscissile, etc.) linking molecules may be used in the practice of the invention. Such molecules or moieties contain one or more chemical bonds which are broken when exposed to light, i.e. the moieties contain at least one photocleavable bond. Photolabile bonds are unstable in the presence of light. Preferably, the linking compounds utilized in the practice of the invention are nontoxic or minimally toxic, although on balance, some toxicity may be tolerated in order to achieve the increased benefit of focused delivery of the drug to a particular location, and the consequent lack of side effects of drug activity at undesirable locations or in non-targeted cells. Exemplary linkages/linking molecules include but not limited to: nitrobenzyl, nitroveratryl, nitrodibenzofuran, nitropiperonyloxymethyl, (coumarin-4-yl)-methyl, quinoline, o-hydroxycinnamate; o-nitrophenethyl, nitroindole, biphenyl-donor-acceptor, salicyl alcohol, p-hydroxyphenacyl, benzoin, cobalamin, etc.

Exemplary photolabile linkers that may be employed in the invention are illustrated in FIG. 3A-G. In FIG. 3A-G, A represents the site of attachment for a e.g. hydrophilic moiety as described herein; X is, for example, N, O, S, carbamate, carbonate and is the site of attachment of the membrane permeable e.g. hydrophobic drug; Y is generally H, C—R, O—R, or H—R, where R=aryl or alkyl or hydrogen substituents; and Z is typically H, halogen, OR where R=aryl or alkyl or hydrogen substituents or one or more additional aromatic rings; and each of A, X, Y and Z may be (independently) present one or more times, e.g. from about 1-10 (1, 2, 3, 4, 5, 6, 7, 8, 9 or 10) times in the linking molecule. In some embodiments, one or more different drugs may be attached to a single prodrug conjugate.

Activation of Photocaged Prodrugs

After a photocaged prodrug is administered to a subject, a location of interest within the subject which contains the prodrug, (the location generally being extracellular e.g. in the circulatory or lymphatic system, or at any location that is accessible to the prodrug), is exposed to light of a wavelength suitable to cleave the particular linkage that was used to form the prodrug. Such exposure causes release of the active drug from the conjugate, whereupon it encounters and enters cells, usually in the adjacent area. Exposure of the photolabile prodrugs may be carried out by any of several methods using suitable equipment. Those of skill in the art will recognize that the light that is applied must contain wavelengths that are capable of reacting with and breaking the particular photolabile linker that is present in the prodrug. For example,

| Linker class: | Range | Preferable wavelength |
| --- | --- | --- |
| Nitrobenzyl-type | 300-380 | 370 nm |
| Nitroindolyl | 300-380 | 370 nm |
| Benzoin | 275-360 | 320 nm |
| Amino coumarin-4-yl-methyl | 325-425 | 400 nm |
| Biphenyl donor acceptor | 360-440 | 400 nm |
| Cobalamin | 360-600 | 560 nm |
| o-hydroxycinnamate | 300-400 | 370 nm |

In certain cases, where the two-photon absorption cross section is high linkers may be cleaved at wavelengths twice the preferable wavelengths stated above. For example biphenyl-donor-acceptor molecules such as: 2,7-bis-{4-nitro-8-[3-(2-propyl)-styryl]}-9,9-bis-[1-(3,6-dioxaheptyl)]fluorene, 2-(4'-(bis(carboxymethyl)amino)-4-nitro-[1,1'-biphenyl]-3-yl)propan-1-ol, 2-(4'-(bis((2-methoxyethoxy)ethyl)amino)-4-nitro-[1,1'-biphenyl]-3-yl)propan-1-ol, can be activated at 800 nM, and o-hydroxycinnamate derivatives such as the julolidine or piperonyl derivatives can be activated at 740 nm.

In some embodiments, the light source may be an optical fiber light source based on any of various types of lamps such as a laser, halogen, xenon, metal-halide, mercury, etc., as well as various apparatuses and methods designed to provide light from such sources, e.g. those described in U.S. Pat. No. 8,175,687 (Kang, et al.), U.S. Pat. No. 8,267,922 (Hodge, et al); U.S. Pat. No. 8,252,033 (Tucker, et al); U.S. Pat. No. 8,246,666 (Pressler, et al); U.S. Pat. No. 8,069,857 (Chung, et al); U.S. Pat. No. 7,513,906 (Passy, et al); the complete contents of each of which is hereby incorporated by reference. In some embodiments, the light energy is applied externally, e.g. over or at the skin of the subject being treated, and wavelengths capable of penetrating the skin are transmitted there through and thus used to photocleave the prodrug molecules under or in proximity to the skin. In other embodiments, light sources may be inserted into or through a cavity of the body (mouth, urethra, esophagus, vagina, threaded through a blood vessel, etc.) or via a surgical incision in order to access tissue and/or cells that are targeted for irradiation.

Light exposure is generally performed from a period of time ranging from about 1 minute to several (e.g. 1, 2, 3, 4, or 5) hours, and may generally be in the range of from about 5 to about 60 minutes. Delivery of light may be continuous during the period, or may be pulsed at short intervals (e.g. a few milliseconds per pulse). Light energy in the range from about 50 to about 1000 J/cm$^2$ of light array fluence in the range from about 5 to about 50 mW/cm of light array may be delivered to the treatment site (e.g. see U.S. Pat. No. 8,235,975, Chen, et al), the complete contents of which is herein incorporated by reference). A single exposure may suffice or multiple exposures may be warranted. In some embodiments, after a single step of administering, the prodrug may remain in circulation (e.g. over a period of several hours or longer), and multiple exposures may occur at timed, spaced apart intervals during that time, e.g. hourly, every few hours, etc. Alternatively, light exposure may be undertaken at various time intervals after additional steps of administration, e.g. daily, weekly, biweekly, etc., over a period of months. The details of such treatment protocols are generally developed during or taking into account the results of clinical trials, and may be modified by a skilled practitioner on a case by case basis. Guidance may be found, for example, in: Morton et al., British Journal of Dermatology 2008 159:1245-1266; and Panjehpour and Overholt, Lasers in Surgery and Medicine 2006 38:390-395.

II. Reversible (Switchable) Peptide Conjugates

In other embodiments, conjugates containing at least one drug of interest chemically attached to a peptide are provided, the peptide having the characteristic of being membrane impermeable in the dark and membrane permeable when exposed to light. In some embodiments, the switch is "one way" in the presence of light (to a membrane permeable state) and in other embodiments, the conformation may "flicker" between membrane permeable and membrane impermeable states in the presence of light. However, only the membrane permeable forms are well-adapted to enter the cell and/or cause the conjugate to enter the cell.

Components of Reversible Peptide Conjugates

Suitable hydrophobic drugs for delivery via reversible peptide conjugates include but are not limited to limited to:
1) cancer drugs such as doxorubicin, epirubicin; vinca alkaloids; 5-fluororacil; taxol; auristatins; maytansine, mertansine and derivatives thereof; tubulysins; camptothecin; didemnins; cisplatin; methotrexate; calecheamycin; and analogs and derivatives of the above;
2. Acne vulgaris drugs such as Isotretinoin, doxycycline and other tetracycline antiobiotics, trimethoprim, sulfamethoxazole, azithromycin
3. Psoriasis drugs such as Vitamin A derivatives (like tazarotene), methotrexate, cyclosporin, hydroxyurea, thioguanine, corticosteroids
4. Actinic keratosis drugs such as 5-fluoro uracil and imiquimod
5. Atherosclerosis drugs; etc.

Any drug that is capable of traversing the cell bilayer and which is attachable to a linking compound as described herein, may be used in the practice of the invention.

Moreover, in some embodiments, the drug of interest is not membrane permeable but is rendered membrane permeable by attachment to a switchable peptide. Examples include protein toxins like diphtheria toxin, ricin, gellonin and the like as well as peptide toxins.

Peptides which may be used in the formation of the switchable peptide conjugates are generally from about 10 to about 25 amino acids in length, and are generally capable of forming an α-helix. When formed into an α-helix, typically one side or face (e.g. on one surface or half) of the helix contains a high percentage (e.g. about 35% to about 50%) of surface exposed side chains of positively charged residues such as Arg, Lys, H is (at some pH values). In some embodiments, the peptides are "arginine rich" i.e. the peptides contain about 20-50% arginine residues. The peptide may also contain one or more other residues that are associated with the ability to form α-helices (e.g. alanine, 2-aminoisobutyric acid), or which at least do not prevent α-helix formation. In an exemplary embodiment, the secondary structure of such a peptide is α-helical and one face of the helix contains an arginine patch, i.e. of the side chains exposed on a face, at least 33% of them are from an Arg residue.

The peptides also generally contain a switchable element that reacts to light, e.g. by switching from one isomeric form to another. A consequence of such a switch is that the relative spatial disposition of neighboring or adjacent components (e.g. amino acid residues) may also be changed, e.g. switching may alter the propensity of the peptide to form an α-helix. In some embodiments, a cis conformation of the switching element promotes helix formation and activity while a trans conformation promotes a non-helical inactive peptide state. Upon formation of the helix, the peptide drug conjugate has enhanced cellular permeability either by passive diffusion or endocytosis, leading to activity. According to the present invention, in some embodiments, the change in conformation advantageously causes the switch itself to undergo changes in cellular permeability due to changes in its own polarity. As a result, the switch becomes membrane permeable to a degree which permits the entire complex to cross the lipid bilayer and enter cells either by passive diffusion or by endocytosis.

Exemplary switchable elements include but are not limited to those which undergo a cis to trans conformational change upon exposure to light such as: azobenzene; modified azobenzenes (such as 4,4'-diamino azobenzenes) and those discussed in U.S. Pat. No. 7,750,130 (Han, et al), U.S. Pat. No. 5,233,010 (McGhee, et al), and U.S. Pat. No. 4,974,941 (Gibbons, et al), the complete contents of each of which is hereby incorporated by reference; stilbenes which switch from cis to trans conformations (e.g. 4,4'-diaminostilbenes)); hemithioindigos which switch from cis to trans conformations. Possible switching elements that do not operate by a cis-trans conversion include but are not limited to: spiropyrans, which switch from a ring closed to a ring-opened form, diarylethenes, which switch from a ring closed to a ring-opened form, and fulgides and fulgimides, which switch from a ring closed to a ring-opened form.

The reversible peptides also contain at least one site of attachment for a drug of interest, e.g. a membrane permeable drug as described herein. Those of skill in the art will recognize that peptides naturally contain reactive groups that may be used as points of attachment for other entities, e.g. atoms which react with atoms of a drug of interest and form a chemical bond, thereby attaching the drug to the peptide by a covalent bond. Exemplary atoms include but are not limited to: sulfur of Cys residues; nitrogen of the N-terminus, nitrogen of lysine residues, carbon of the C-terminal carboxylic acid, carbon of the side chain carboxylic acids of aspartic acid and glutamic acid, phenolic oxygen of tyrosine. Other linkage types include residues not typically found in standard peptides but that can be introduced during the course of synthesis, in particular including bioorthogonal reactions like (azide-alkyne cycloadditions, dipolar cycloadditions, Staudinger ligations, and diels-alder reactions, etc. In some embodiments, the attachment of the peptide to the drug is via a protease cleavable linkage. For example, the linkage valine-citrulline-p-aminobenzyloxy is susceptible to cleavage by the lysosomal protease cathepsin B. Other exemplary protease cleavable linkages that may be used in the practice of the invention include but are not limited to, for example, those listed in Table 1 below (see the website located at onlinelibrary.wiley.com/doi/10.1002/cmdc.200700159/full).

Once the conjugate is within the cell, protease cleavage releases the drug in an active form as described above for the photocaged embodiment, e.g. a form that can carry out the intended or desired biological activity, such as killing tumor cells.

above 600 nm afford the best results, with penetration depth approaching 0.5 cm or greater attainable with near IR wavelengths in certain tissues. Standard azobenzene elements switch at 370 nm, but also have some two-photon photoswitching capability at 740 nm. Other azobenzene photoswitches operate at wavelengths of up to 537 nm. Generally, in the practice of the invention, wavelengths in a range of from about 350 to about 800 nm may be used, e.g. when two photon switching is considered.

Generally, for a particular step of light administration, one (a single) wavelength or a narrow range of wavelengths (e.g. a 5-10 nm band) will be employed. However, irradiation at multiple selected wavelengths or combinations of wavelengths is also contemplated. Most photoswitches can also be reverted partially, but typically not completely, back to their dark state using a different wavelength of light. This gives the option of turning the permeability of the molecules off by using this different wavelength, and methods encompassing this option are contemplated herein. The exact wavelengths of light are typically 50-100 nm longer than those required to convert from the dark adapted to the excited state.

TABLE 1

| Enzyme | Function | Substrate examples |
|---|---|---|
| Cathepsin B (EC 3.4.22.1) | Lysosomal | Arg-Arg, Leu, |
| Cathepsin H (EC 3.4.22.16) | degradation of | Ala-Leu, |
| Cathepsin L (EC 3.4.22.15) | proteins | Gly-Leu-Phe-Gly, |
|  |  | Gly-Phe-Leu-Gly, |
|  |  | Ala-Leu-Ala-Leu |
| Cathepsin D | Degradation of | Phe-Ala-Ala-Phe($NO_2$)-Phe-Val-Leu-OM4P, |
| (EC 3.4.23.5) | extracellular matrix | Bz-Arg-Gly-Phe-Phe-Pro-4MβNA |
| Plasmin (EC 3.4.21.7) | Fibrinolysis, | D-Val-Leu-Lys, |
|  | degradation of blood | D-Ala-Phe-Lys, |
|  | plasma proteins | D-Ala-Trp-Lys |
| uPA (EC 3.4.21.73)[a] | Activation of plasmin | Gly-Gly-Gly-Arg-Arg |
| tPA (EC 3.4.21.68)[b] | formation | Arg-Val |
| Prostate-specific antigen | Liquefaction of | Mu[c]-His-Ser-Ser-Lys-Leu-Gln-Leu, |
| [PSA (EC 3.4.21.77)] | semen | L-377,202[d] |
| Matrix metalloproteases | Degradation of | Ac-Pro-Leu-Gly-Leu, |
| [MMP-2 (EC 3.4.24.24), | extracellular matrix | Ac-ãE-Pro-Cit-Gly-Hof[e]-Tyr-Leu, |
| MMP-9 (EC 3.4.24.35)] | and collagens | Gly-Pro-Leu-Gly-Ile-Ala-Gly-Gln |
| â-Glucuronidase | Hydrolysis of | Glucuronide moieties |
| (EC 3.2.1.31) | glucuronide moieties |  |
|  | from proteins |  |
| Carboxylesterases | Hydrolysis or | Ester or carbamate moieties |
| [CES1/CES2 (EC 3.1.1.1)] | transesterification of |  |
|  | drugs or xenobiotics |  |

[a]Urokinase-type plasminogen activator.
[b]Tissue-type plasminogen activator.
[c]Mu = morpholinocarbonyl.
[d]L-377,202 = N-glutaryl-(hydroxypropyl)-Ala-Ser-cyclohexylglycyl-Gln-Ser-Leu.
[e] Hof = homophenylalanine.

The peptides may be stabilized with respect to secondary structure, for example, by crosslinking, cyclization (e.g. by hydrocarbon stapling), or by the addition of capping groups known to template (foster, increase bias toward, etc.) helicity at the N- and C-terminus. The peptides may also be stabilized with respect to proteolytic cleavage, e.g. by introducing one or more D or N-methyl amino acids into the sequences, except that in some embodiments, cleavage at the peptide-drug linkage is desirable as described above.

Wavelength may be an important consideration in therapy that involves interaction of tissues with light. Tissue penetration depth is quite dependent on tissue type, but the absorbance profiles of different tissues are similar, with a general trend towards better penetration with longer wavelengths (with reduction in penetration near the absorbing wavelengths of hemoglobin at 425 and 550 nm). Wavelengths Light is usually delivered using protocols and sources as described above for photolabile prodrugs.

Pharmaceutical Compositions and Administration Thereof (for Both Photocaged Prodrug and Reversible Peptide Embodiments)

The present invention provides pharmaceutical compositions comprising one or more substantially purified conjugates as described herein and a pharmacologically suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other biologically active agents, e.g. other drugs or active agents. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent/conjugate in the formulations may vary. However, in general, the amount in the formulations will be from about 1-99%.

The compositions (preparations) of the present invention may be administered by any of the many suitable means which are well known to those of skill in the art, including but not limited to intravenously, by injection, inhalation, orally, intravaginally, intranasally, topically, as drops, sprays, etc. Administration may be systemic or local, e.g. intratumorally, or into a body cavity, or into an area exposed by a surgical incision, etc. In preferred embodiments, the mode of administration is intravenously or by injection. In addition, the compositions may be administered in conjunction with other treatment modalities suitable for treatment of the disease of interest that is being treated, such as substances that boost the immune system, various chemotherapeutic agents, antibiotic agents, and the like.

The amount of active agent that is administered will vary and is dependent on factors that are well known to those of skill in the art, usually medical professionals such as physicians. Factors may include the disease being treated, the drug or drugs that is/are being used, the age, gender and physical condition of the patient, patient ethnicity and/or genetic profile, etc.

Subjects to whom the conjugates are administered are generally mammals, and are frequently humans, although this need not always be the case. Veterinary and non-mammalian applications of the invention are also contemplated.

Treatment of Diseases or Conditions (For Both Photocaged Prodrugs and Reversible Peptide Complexes)

The invention also provides methods of treating diseases and conditions in a patient in need thereof, and of providing membrane permeable drugs to cells of a patient in a targeted, selective manner. The diseases and conditions are those which are treatable using one or more membrane permeable drugs or agents. In some embodiments, the disease is cancer and the cells to which the membrane permeable drug is provided are cancer cells, which may be located in a tumor, i.e. the targeted location of interest may be a tumor. The methods may comprise a step of identifying a patient having or susceptible to developing a disease or condition that is treatable by a membrane permeable drug that can be temporarily rendered membrane impermeable by the methods described herein. The methods include a step of administering a complex as described herein to the patient, and then exposing an area of interest (a targeted location) in or on the patient's body to a wavelength of light suitable to i) cleave the light-labile bond of the complex, thereby releasing active drug at the targeted location; or ii) cause conversion of a membrane impermeable peptide of the complex to a membrane permeable form.

Manufacture of the Conjugates of the Invention

The invention also encompasses methods of manufacturing the conjugates described herein. For the conjugates from which the drug is released prior to entry into the cell, the methods involve chemically attaching a membrane impermeable moiety of interest to a membrane permeable drug of interest via a photo labile entity that contains a photo-cleavable bond. For the reversible peptide conjugates of the invention, the methods involve chemically attaching a peptide of interest whose membrane permeability is switchable (reversible) upon exposure to light to a membrane permeable drug of interest.

The following examples are intended to illustrate various embodiments of the invention but should not be construed so as to limit the invention in any way.

EXAMPLES

Example 1

Photocaged Permeability: a new strategy for controlled drug release: Light is used to release a drug from a cell impermeable small molecule, uncloaking its cytotoxic effect on cancer cells.

Off-target toxicity plagues conventional cancer chemotherapy. One strategy to enhance selectivity of anti-cancer drugs involves unmasking the cytotoxicity of a molecule in the vicinity of the tumor[1]. This type of activation can be mediated by enzymes[2,3], changes in pH[4], or exogenous factors such as temperature[5] or light[6-8].

Light is an ideal external stimulus since it provides a broad range of adjustable parameters[9] that can be optimized for biological compliance. Several approaches that use light for biomolecular activation have been reported[10-15]. One established method to enable selectivity of drug action using light is photodynamic therapy (PDT). In PDT,[16,17] light activation of a photosensitizer generates cytotoxic singlet oxygen killing only illuminated cells. PDT is currently used in several types of malignancies[16] including skin, lung, esophageal, bladder, head and neck, and prostate cancer. A related strategy, photochemical internalization[18,19], also uses photosensitizers. In this case, the photosensitizers are used to release macromolecular cytotoxins from endosomes, enabling their entry into the cytosol. However, these approaches suffer from disadvantages[20], including unpredictable drug uptake rates, the limited diffusion and lifetime of $^1O_2$, and the requirement for moderate levels of $O_2$ which may not always be available in the tumor environment.

In this Example, we report a new light-targeted drug delivery system, which operates independently of the creation of $^1O_2$. The basis of the system is the attachment of a cell impermeable small molecule to a drug via a linker that can be removed in presence of light, allowing cellular entry (FIG. 4). We call this new strategy photocaged permeability (PCP)[21].

More specifically, we report the controlled release of the anticancer drug, doxorubicin (Dox), upon illumination. To prevent entry of Dox in the dark we attached Dox to EDANS, a small fluorophore, chosen because it contains a sulfonic acid moiety known to hinder cellular entry[22]. To connect Dox to EDANS we utilized a light-cleavable nitroveratryl[23] linker. The nitroveratryl moiety has been used previously as a photocaging group for a wide variety of biomolecules[24]. The chemical structures of Dox and EDANS are shown in FIG. 5.

The synthesis (Scheme 1) began with commercially available nitroveratryl carboxylic acid (1). The N-hydroxy succinimide ester was prepared followed by coupling with propargylamine to give amide (2). This compound was converted to the p-nitrophenyl carbonate which was then treated with doxorubicin[3] to generate photocaged doxorubicin carbamate (3). EDANS was coupled with azido benzoic acid (5) and was finally attached to the photocage using click chemistry to generate the final Dox-EDANS conjugate (6).

Scheme 1: Synthesis of photocaged-cell impermeable drug conjugate.

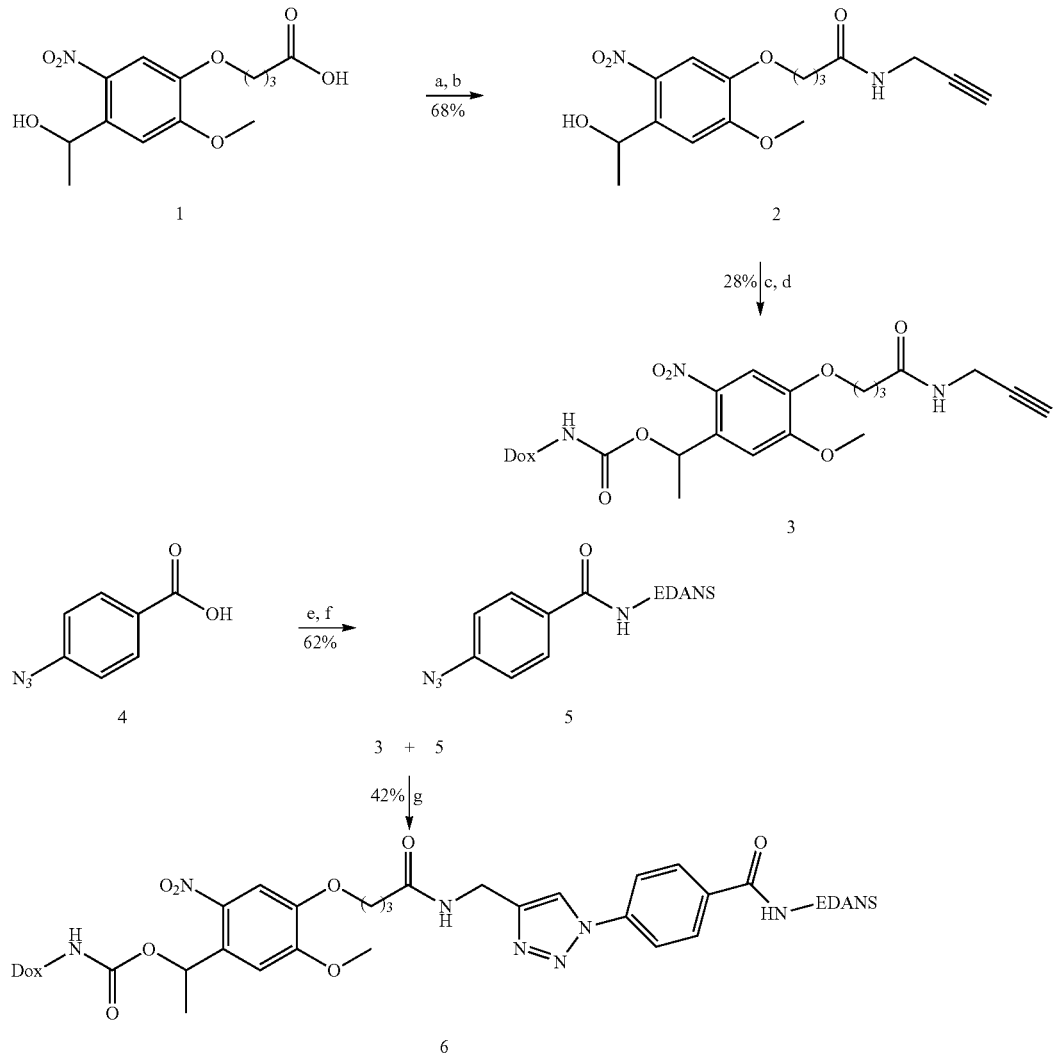

Reagents and conditions: (a) NHS, EDC•HCl; (b) propargylamine, Et$_3$N; (c) bis p-nitrophenylcarbonate, Et$_3$N; (d) doxorubicin HCl•, Et$_3$N; (e) NHS, EDC•HCl (f) EDANS, Et$_2$N(iPr)$_2$; (g) CuSO$_4$•5H$_2$O, sodium ascorbate, tris-(benzyltriazolylmethyl) amine, (1:1) (DMSO: water)

The photolytic release of doxorubicin from the drug conjugate was analyzed using HPLC. The drug conjugate was dissolved in PBS buffer and was exposed to UV light at 365 nm (9.0 mW/cm$^2$). Aliquots of the reaction mixture were collected at various times and were analyzed on RP-HPLC. During the course of reaction, the peaks corresponding to the Dox-EDANS conjugate disappeared with concomitant increase in the intensity of a peak with the same retention time as Dox (see FIG. 6), confirming time-depended drug release in the presence of light.

We then investigated whether the attachment of EDANS to Dox via the veratryl linker would enable drug delivery. JH-EsoAd1 cells, a Barrett's esophagus associated adenocarcinoma cell line[25], were incubated with Dox-EDANS in the dark or with illumination. Cell permeability was measured with flow cytometry; upon illumination a significant enhancement of cellular Dox fluorescence was observed (FIGS. 7A and B; FIG. 8A-B). This enhancement was mirrored in confocal studies with the same cell line (not shown)—only light-treated cells show significant Dox fluorescence in the nucleus, where it is known to accumulate[26].

Figure 9:
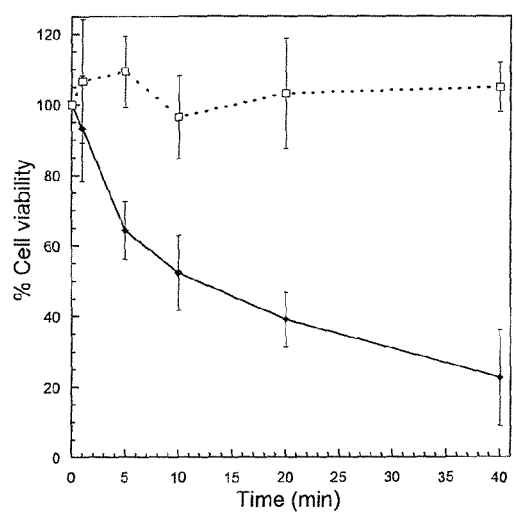
FIG. 9. Light-dependent cytotoxicity of Dox-EDANS. Cells were treated with 10 μM of Dox-EDANS with (solid diamonds) or without (open squares) light for the specified times. The fraction of surviving cells was evaluated using the absorbance of the formazan product of MTT reduction. Error bars denote one standard deviation from the mean.
Figure 10:
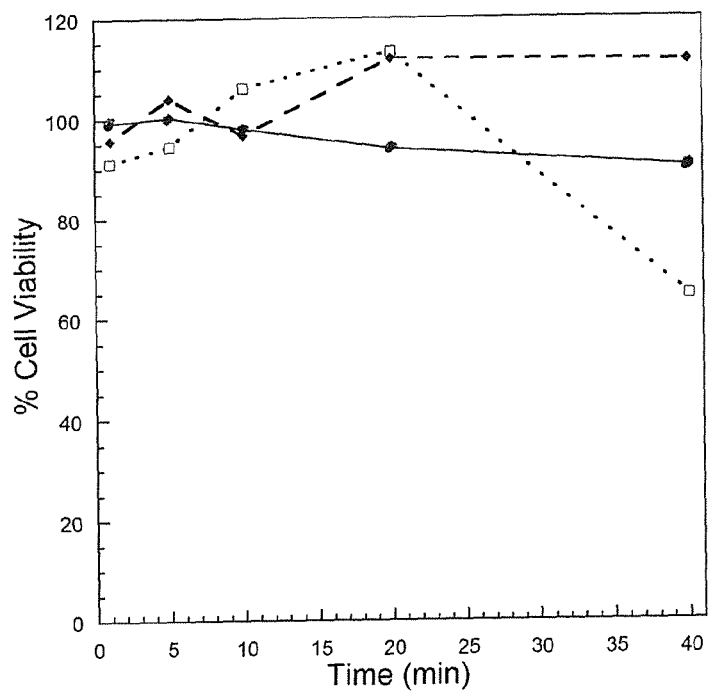
FIG. 10. Effect of light and EDANS on cell survival. JHEsoAd1 cells were treated with EDANS in the dark (diamonds), EDANS+light (open squares) (9 mW/cm$^2$) or light alone (circles) for the specified times. Cell survival was determined using the MTT assay. Each data point was taken from a minimum of six replicate experiments. Error bars are omitted for clarity.

With permeability enhancement established, we proceeded to investigate the extent to which the release of Dox with light would lead to enhanced cellular toxicity. Indeed, increased illumination lead to decreased survival as measured by an MTT assay (FIG. 9). Survival of cells treated with EDANS-Dox in the dark was equivalent to controls with no drug added. Moreover, treatment with light alone at the same dose was not cytotoxic (See FIG. 10).

Figure 11:
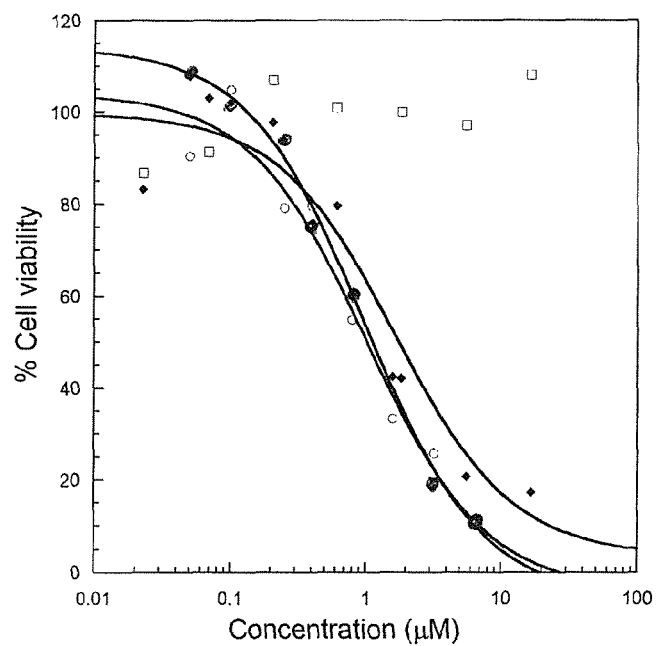
FIG. 11. Concentration-dependent toxicity of compounds on JH-EsoAd1 cells. % cell viability was plotted for JH-EsoAD1 cells at various concentrations of EDANS-Dox in the dark (open squares) or with light (black diamonds), and unconjugated Dox in the dark (open circles) or with light (solid circles). Experiments were performed in at least six replicates. Error bars are omitted for clarity. The lines are plots of the curve fits of the relevant data to the equation: Y=M1+(M2−M1)/(1+X/M3). The constant M3 describes the IC$_{50}$ value.
Figure 12:
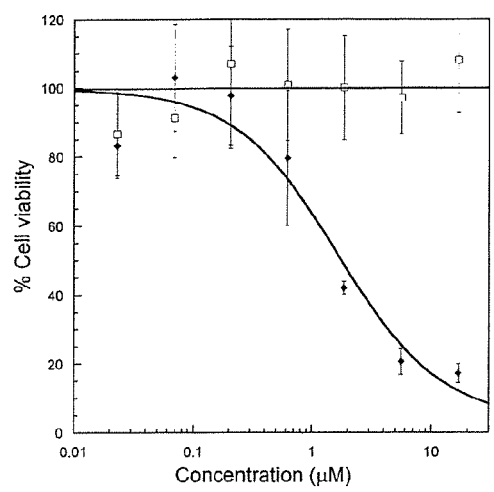
FIG. 12. Concentration dependent Light-stimulated cytotoxicity. Cells were treated with EDANS-Dox at various concentrations in the dark (open squares) or with UV light for 20 minutes (black diamonds). The fraction of surviving cells relative to no drug controls was evaluated using the absorbance of the formazan product of MTT reduction. Error bars denote one standard deviation from the mean.

Finally, we sought to compare the concentration dependence for our method vs. Dox alone. We first measured the IC$_{50}$ of Dox alone with the JH-EsoAd1 cells and found it to be 1.0±0.4 µM (see FIG. 11). As expected by PCP, EDANS-Dox was not toxic to the cells in the dark at the highest value tested (16 mM). However, illumination of EDANS-Dox (365 nm, 9.0 mW/cm$^2$) leads to cytotoxicity with an IC$_{50}$ of 1.6±1.0 µM (FIG. 12), comparable to that of Dox alone. Based on our FACS study (FIG. 8), we deduce that this enhanced cytotoxicity is caused by efficient light-stimulated release of free Dox from the impermeable EDANS.

In conclusion, we have developed a new and efficient strategy for drug release based on photocaged permeability (PCP). In this first report, we have focused on applying PCP to the light-stimulated delivery of Dox into esophageal adenocarcinoma cells. In principle, the PCP approach could be applied to any small, cell permeable molecule that has a free amine, hydroxyl, or carboxylic acid group for attachment of the veratryl-EDANS molecule. Further experiments will focus on use of other light-scissile linkers that can operate at longer wavelengths that are able to penetrate farther into tissues, as well as the use of other molecules that block permeability.

Materials

All reagents were purchased from Sigma-Aldrich, Fisher Scientific or TCI America unless otherwise specified and were used as received. Dimethyl Formamide (DMF) used as a solvent for chemical synthesis was dried by vacuum distillation. All reactions were carried out in oven dried glassware and under Ar or N$_2$ atmosphere. The reactions were carried out in foil-wrapped flasks, protected from light. Flash chromatography was performed using Flash Silica Gel (32-63µ). $^1$H NMR/$^{13}$C spectra were recorded on 400 MHz Bruker AVANCE and 300 MHz Varian instruments. HPLC purification was carried out using a Shimadzu Prominence system using Vydac (218TP C18 5µ) column using 0.1% TFA in acetonitrile and water as eluents and was monitored at $\lambda_{max}$=480 nm. M/S data was collected using Micromass MALDI/TOF (positive and negative modes). The UV lamp used in all studies consisted of a simple aquarium light fixture containing two Philips PL-S 9w/2P BLB bulbs.

The Esophageal cancer cell line (JH-EsoAd1) was cultured at 37° C. and in a humidified atmosphere of 5% CO$_2$ in RPMI 1640 medium supplemented with 10% fetal bovine serum (FBS). For 96 well plate experiments, the JH-EsoAd1 cells were seeded at 4450 cells/well in 100 uL of media in 96 well plates; experiments were carried out one day after seeding. MTT assays were analyzed using a Bio-Tex µQuant plate reader at 562 nm. FACS was performed BD FACS Aria II using BD FACS Diva software at the VCU Flow Cytometry Core Facility. A minimum of 20,000 cells within the gated region were analyzed. Confocal microscopy images were acquired at room temperature with a Leica confocal laser scanning microscope.

LIST OF ABBREVIATIONS

NHS N-Hydroxysuccinimide
EDC. HCl (1-Ethyl-3-(3-dimethylaminopropyl)carbodiimide hydrochloride)
EDANS. HCl (5-((2-Aminoethyl)amino)naphthalene-1-sulfonic acid) hydrochloric acid
Dox Doxorubicin Hydrochloride
TBTA tris-(Benzyltriazolylmethyl)amine
TFA Trifluoroacetic acid
MTT (3-(4,5-Dimethylthiazol-2-yl)-2,5-diphenyltetrazolium bromide
Detailed Scheme for the Synthesis of EDANS-Dox

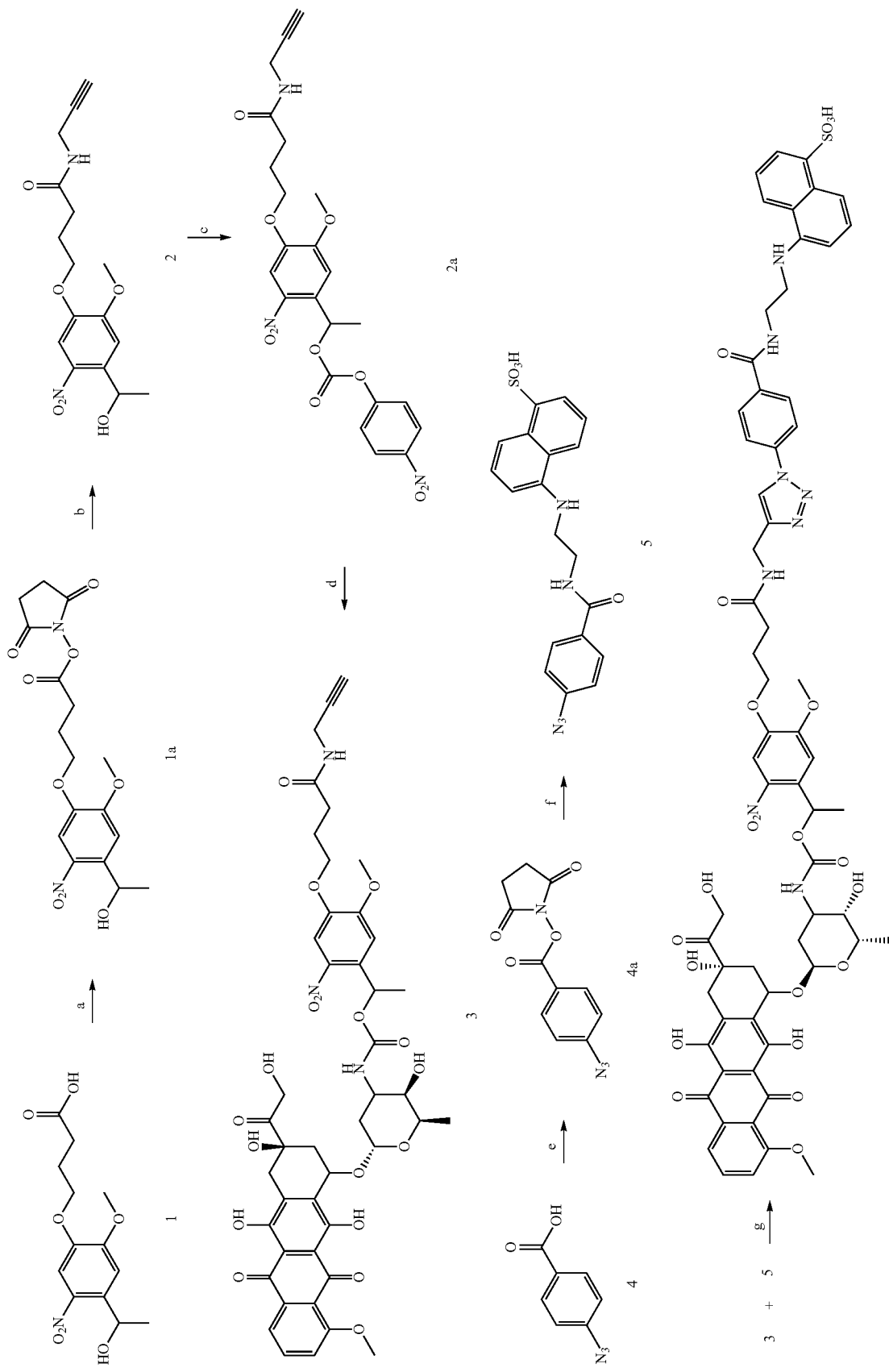

-continued a) NHS, EDC·HCl, DMF b) propargylamine, N(Et)₃, DMF c) Bis 4-nitrophenol carbonate, N(Et)₃, DMF d) doxrubicin·HCl, N(Et)₃, DMF e) NHS, EDC·HCl, DMF f) EDANS·HCl, N(ipr)₂Et, DMF g) CuSO₄·5H₂O, sodium ascorbate, TBTA, (1:1) DMSO: Water Experimental Methods

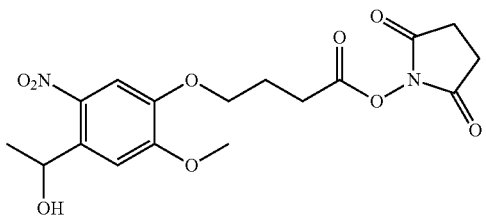 [SMILES: COc1cc(C(C)O)c([N+](=O)[O-])cc1OCCCC(=O)ON1C(=O)CCC1=O]

Synthesis of 2,5-dioxopyrrolidin-1-yl 4-(4-(1-hydroxyethyl)-2-methoxy-5-nitrophenoxy) butanoate (1a)

4-(4-(1-hydroxyethyl)-2-methoxy-5-nitrophenoxy) butanoic acid (1) (200 mg, 0.67 mmol) was dissolved in 10 ml of DMF and stirred for 5 minutes at 0° C. To this mixture, EDC-HCl (1.5 eq., 156 mg, 1.0 mmol) was added followed by NHS (1.5 eq., 115 mg, 1.0 mmol). The reaction was stirred under $N_2$ atmosphere in the dark at 0° C. for approximately 1 h and then at rt for 15 h. DMF was removed in vacuo. To this mixture, 30 ml of EtOAc was added followed by extraction with water (3×20 ml). The organic layer was dried with $MgSO_4$, filtered and the solvent was removed under reduced pressure. The product obtained was single spot on TLC and was taken to the next step without purification.

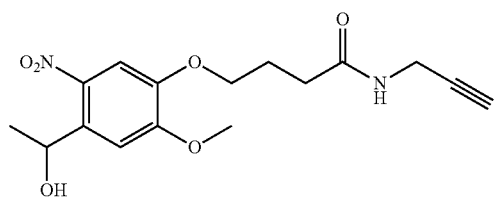 [SMILES: C#CCNC(=O)CCCOc1cc([N+](=O)[O-])c(C(C)O)cc1OC]

Synthesis of 4-(4-(1-hydroxyethyl)-2-methoxy-5-nitrophenoxy)-N-(prop-2-yn-1-yl) butanamide (2)

1a (250 mg, 0.63 mmol) was dissolved in 5 ml of DMF and stirred for 5 minutes. To this solution triethylamine (2 eq., 175 µL, 1.26 mmol) was added dropwise followed by propargylamine (2 eq., 70 mg, 1.26 mmol). The reaction was stirred overnight at rt, under nitrogen gas in the dark. Then, DMF was removed under low vacuum. To the resulting pale yellow oil was added EtOAc (25 ml), followed by washing with water (3×20 mL). The organic layer was dried over $MgSO_4$ and filtered; the solvent was removed and purified using column chromatography (100% EtOAc) to yield pale white solid (153 mg, 72%).

$^1$H NMR (CDCl$_3$, 400 MHz):
δ=7.57 (s, 1H, Ar—H), 7.31 (s, 1H, Ar—H), 5.93 (br. s, 1H, N—H), 5.55-5.58 (m, 1H, CH$_3$—CH), 4.12 (t, 2H, —CH$_2$, J=8.0 Hz), 4.06 (dd, 2H, —CH$_2$, J$_{ab}$=4.0 Hz, J$_{ac}$=4.0 Hz), 3.9 (s, 3H, OCH$_3$), 2.45 (t, 2H, —CH$_2$—, J=8.0 Hz), 2.21 (br.s, 1H, —CH), 2.2 (m, 3H), 1.56 (d, 3H, —CH—I$_3$, J=4.0 Hz).

$^{13}$C NMR (CDCl$_3$, 300 MHz) δ=24.7, 24.9, 29.3, 32.7, 56.5, 65.7, 68.6, 71.7, 79.8, 108.9, 109.2, 137.9, 139.4, 146.8, 154.0, 172.5.

MS (MALDI-TOF+): calculated. (M+Na$^+$) 359.12. found=359.27.

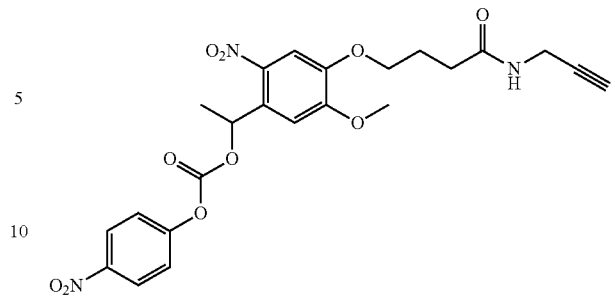

Synthesis of 1-(5-methoxy-2-nitro-4-(4-oxo-4-(prop-2-yn-1-ylamino)butoxy)phenyl)ethyl (4-nitrophenyl) carbonate (2a)

To a stirred solution of 2 (100 mg, 0.30 mmol) in dry DMF (10 ml) was added triethylamine (83 µL, 2 eq., 0.59 mmol) followed by bis(4-nitrophenyl)carbonate (271 mg, 3 eq., 0.89 mmol). The solution was stirred overnight in the dark at rt after which it was cooled and acidified with 20 mL of 1% HCl. The mixture was extracted with 30 mL of EtOAc and the organic layer was washed with saturated NaHCO$_3$ (3×20 mL) solution and brine (1×20 mL) and dried over MgSO$_4$. The solution was filtered, concentrated and purified by flash column chromatography (1:1 to 7:3 EtOAc:hexanes) to yield pale yellow colored solid. (81 mg, 54%).

$^1$H NMR (CDCl$_3$, 400 MHz):
δ=8.26 (d, 2H, Ar—H, J=8.0 Hz), 7.61 (s, 1H, Ar—H), 7.36 (m, 2H, Ar—H), 7.12 (s, 1H, Ar—H), 6.53 (q, 1H, CH$_3$—CH, J=8.0 Hz), 5.91 (br. s, 1H, N—H), 4.14 (t, 2H, —CH$_2$, J=8.0 Hz), 4.06 (dd, 2H, —CH$_2$, J$_{12}$=4.0 Hz, J$_{13}$=8.0 Hz), 4.01 (s, 3H, —OCH$_3$), 2.45 (t, 2H, —CH$_2$, J=4.0 Hz), 2.21 (m, 3H), 1.78 (d, 3H, —CH$_3$, J=8.0 Hz).

$^{13}$C NMR (CDCl$_3$, 400 MHz):
δ=21.9, 24.6, 29.2, 32.5, 56.54, 68.49, 71.5, 73.7, 79.5, 108.0, 109.1, 115.7, 121.66, 131.4, 139.9, 145.4, 147.6, 151.4, 154.1, 155.3, 171.8.

MS (MALDI-TOF+): calculated. (M+Na)$^+$=524.13. found=524.29.

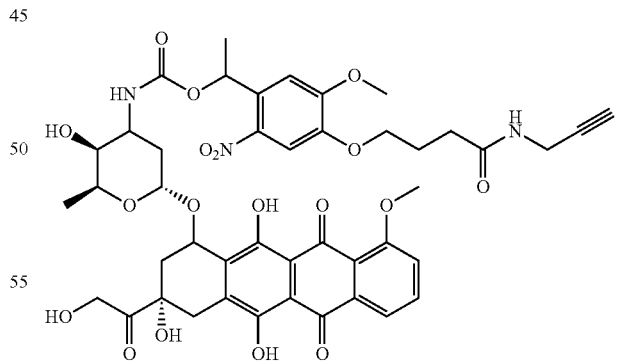

Synthesis of Photocaged Doxorubicin (3)

To a stirred solution of 2a (80 mg, 0.16 mmol) in dry DMF (3 ml) was added triethylamine (45 µL, 2 eq., 0.32 mmol) followed by Dox (44 mg, 0.5 eq., 0.08 mmol). The solution was stirred at rt for 24 h under nitrogen, in the dark. Then, DMF was removed under low vacuum. To this red colored solid, 30 ml of EtOAc was added and washed with water (3×20 ml). The organic layer was dried over MgSO$_4$, filtered and the solvent was removed and purified using column chromatography (silica/EtOAc and then 1:10 MeOH:CHCl$_3$) to yield 52% of a mixture of diastereomers. The resulting solution was purified on RP-HPLC using isocratic elution of 20% organic eluent (0.1% TFA in acetonitrile) for 5 minutes and then using gradient elution from 20% to 70% for 30 minutes. The two diastereomers (D$_{t-1}$ and D$_{t-2}$) eluted at D$_{t-1}$=35.8 and D$_{t-2}$=36.9 min (See ESI FIG. S1). The NMR analysis showed the presence of two products corresponding to the two diastereomers.

$^1$H NMR (DMSO-d6, 400 MHz): (2× means both diastereomeric products had indistinguishable ppm values for those protons)

14.05 (s, 1H), 14.0 (s, 1H), 13.27 (s, 2×1 H), 7.92 (m, 2×2H), 7.66 (m, 1×2H), 7.54 (s, 1H), 7.49 (s, 1H), 7.17 (s, 1H), 7.13 (s, 1H), 6.05 (m, 2×1H), 5.41 (m, 2×1H), 5.21-5.23 (m, 2×1H), 4.95 (m, 2×1 H), 4.78-4.84 (m, 2H), 4.66 (m, 2×1), 4.55 (m, 2×2H), 3.82-4.14 (m, 2×11H), 3.64-3.73 (m, 4H), 3.51 (m, 1×2 H), 3.05 (t, 1H, J=4.0 Hz), 3.08 (t, 1H, J=4.0 Hz), 2.97 (m, 4H), 2.90 (s, 1H), 2.74 (s, 1H) 2.18-2.28 (m, 6H), 1.83-1.85 (m, 4×2H), 1.48 (m, 3×2H), 1.10 (m, 3×2H).

$^{13}$C NMR (DMSO, 400 MHz):

21.92, 27.78, 46.91, 46.99, 56.15, 56.23, 56.26, 56.42, 60.18, 63.7, 66.73, 68.21, 69.74, 72.73, 74.89, 81.21, 100.2, 108.44, 108.66, 110.41, 110.56, 118.8, 118.83, 119.47, 119.73, 128.6, 133.54, 134.4, 135.2, 135.27, 135.98, 139.0, 139.22, 146.65, 146.69, 153.58, 154.37, 155.68, 155.92, 160.64, 171.24, 171.3, 186.22, 213.81.

MS (MALDI-TOF): calculated. (M+Na$^+$) 928.28. found 928.43.

Figure 14:
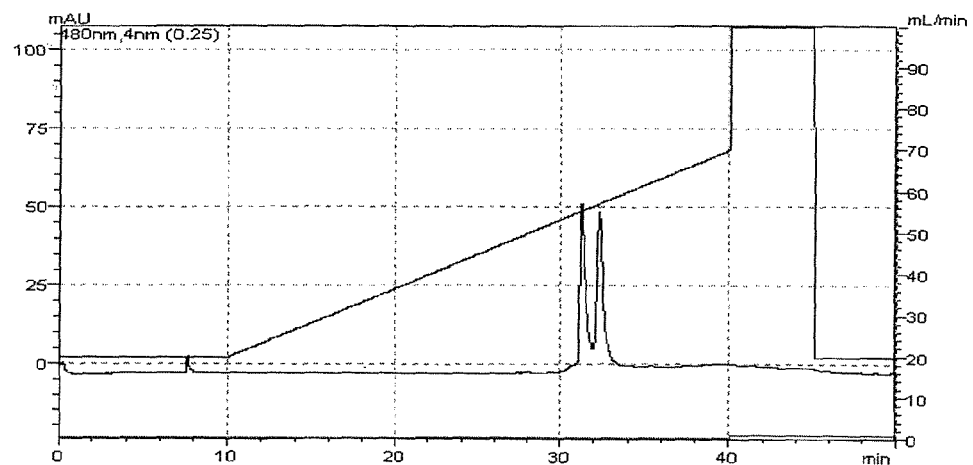
FIG. 14. RP-HPLC analysis of EDANS-Dox (6), using absorbance at 480 nm. The two diastereomers have retention times of 31.25 and 32.28 min.

HPLC Purity analysis: See FIG. 14

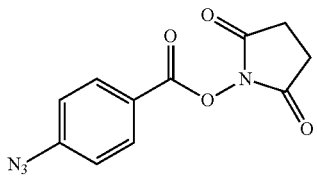 [SMILES: [N-]=[N+]=Nc1ccc(C(=O)ON2C(=O)CCC2=O)cc1]

Synthesis of 2,5-dioxopyrrolidin-1-yl 4-azidobenzoate (4a)

4-azidobenzoic acid (4) (500 mg, 3.065 mmol) was dissolved in 10 ml of DMF cooled to 0° C. To this mixture, EDC.HCl (1.2 eq., 570 mg, 3.678 mmol) was added followed by NHS (1.2 eq., 424 mg, 3.678 mmol). The reaction was stirred in the dark under N$_2$ at 0° C. for approximately 1 h and then at rt for 15 h. DMF was removed in vacuo. This concentrated mixture was dissolved in 30 ml of EtOAc and then extracted with water (3×20 ml). The organic layer was dried over MgSO$_4$, filtered, evaporated and purified using column chromatography (100% EtOAc) to yield 97% of pale yellow colored product.

$^1$H NMR (DMSO, 400 MHz):

δ=8.11 (d, 2H, Ar—H, J=8.0 Hz), 7.36 (d, 2H, Ar—H, J=8.0 Hz), 2.90 (s, CH$_2$, 4H).

$^{13}$C NMR (DMSO, 400 MHz):

δ=25.48, 120.06, 120.46, 131.98, 146.80, 161.06, 170.32.

MS (MALDI-TOF): calculated. (M+Na)$^+$ 283.04. found: 283.28.

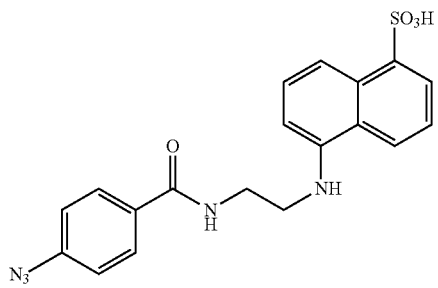 [SMILES: [N-]=[N+]=Nc1ccc(C(=O)NCCNc2cccc3c(S(=O)(=O)O)cccc23)cc1]

Synthesis of 5-((2-(4-azidobenzamido)ethyl)amino) naphthalene-1-sulfonic acid (5)

To a stirred solution of 4a (50 mg, 0.192 mmol, 1.1 eq.) in dry DMF (10 ml) was added EtN(iPr)$_2$ (46 µL, 1.5 eq., 0.262 mmol) followed by EDANS (47 mg, 1 eq., 0.174 mmol). The turbid, brown solution was stirred at rt for 10 h under nitrogen. The solvent was then removed under low vacuum. To the resulting brown, thick oil, 30 ml of CH$_2$Cl$_2$ was added and washed with water (3×20 ml). The organic layer was dried over Na$_2$SO$_4$, filtered and the solvent was removed and purified using column chromatography (silica/15:85 MeOH:CHCl$_3$) to yield 46 mg (64%) of a brown solid.

$^1$H NMR (DMSO, 400 MHz):

δ=8.72 (t, 1H, —CONH—, J=8.0 Hz), 8.07 (d, 2H, Ar—H, J=8.0 Hz), 7.88 (m, 3H, Ar—H), 7.27 (dd, 2H, —CH$_2$, J$_{12}$=8.0 Hz, J$_{13}$=8.0 Hz), 7.21 (dd, 2H, —CH$_2$, J$_{12}$=8.0 Hz, J$_{13}$=8.0 Hz), 7.14 (m, 2H, Ar—H), 6.58 (d, 1H, Ar—H, J=8.0 Hz), 3.54 (m, 2H, —CH$_2$), 2.99 (m, 2H, —CH$_2$—).

$^{13}$C NMR (DMSO, 400 MHz):

δ=25.20, 45.6, 102.7, 115.6, 118.9, 122.3, 126.2, 129.1, 130.1, 130.9, 142.2, 143.71, 143.9, 165.8, 172.7.

MS (MALDI-TOF): calculated. (M+Na)$^+$434.09. found: 434.69.

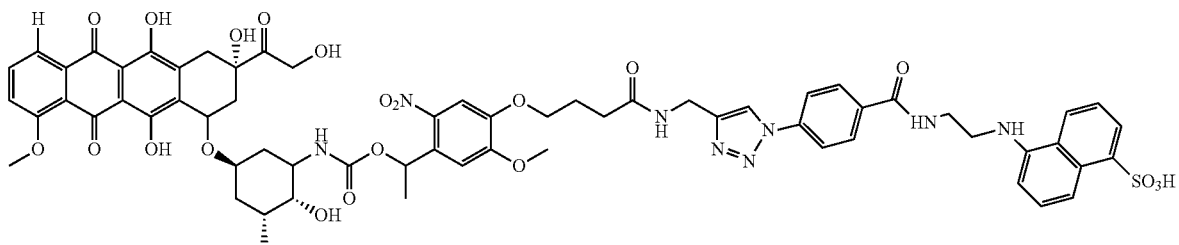

Synthesis of Photocaged-Cell Impermeable Dox. Conjugate (6)

Compounds 3 (50 mg, 0.055 mmol, 1 eq.) and 5 (21.7 mg, 0.05 mmol, 1 eq.) were stirred in 1:1 mixture of water and DMSO (4 mL each). 100 μL (1 mg, 0.005 mmol, 0.1 eq.) of freshly prepared aqueous solution of sodium ascorbate (10 mg/mL) was added to the reaction, followed by 10 μL (0.125 mg, 0.01 eq., 0.0005 mmol) of freshly prepared aqueous solution of copper (II) sulfate pentahydrate (12.5 mg/mL) was added and finally 2.65 mg (0.1 eq., 0.005 mmol) of TBTA was added. The red colored heterogenous mixture was stirred vigorously until the reaction was completed as judged by TLC (1:4 $CH_3OH/CHCl_3$). The reaction mixture was concentrated in vacuo, filtered and the resulting solution was purified on RP-HPLC using isocratic elution of 20% organic eluent (0.1% TFA in acetonitrile) for 5 minutes and then increasing the acetonitrile fraction in gradient fasion from 20% to 70% over 30 minutes. The fractions (3 mL each) were collected into tubes containing 500.1 L of ammonium bicarbonate (2 mg/mL) solution to quench the TFA. The two diastereomers ($D_t$-3 and $D_t$-4) eluted at $D_t$-3=31.25 and $D_{t-4}$=32.28 min (See ESI FIG. S2). The fractions containing the diastereomers were evaporated leaving a red solid (30 mg, 41%). One of the diastereomers ($D_{t-3}$) was isolated for proton NMR analysis.

$^1$H NMR (DMSO, 400 MHz):

δ=14.06 (s, 1H), 13.29 (s, 1H), 8.85 (t, 1H, J=4.0 Hz), 8.72 (s, 1H), 8.44 (t, 1H, J=8.0 Hz), 8.12 (m, 1H), 8.08 (d, 2H, J=8.0 Hz), 8.02 (d, 2H, J=8.0 Hz), 7.91-7.94 (m, 2H), 7.66-7.68 (m, 1H), 7.54 (s, 1H), 7.24-7.34 (m, 3H), 7.15 (s, 1H), 7.0-7.02 (m, 1H), 6.64 (d, 1H, J=8.0 Hz), 6.05 (m, 1H), 5.41 (m, 2H), 5.22 (s, 1H), 4.95 (m, 1H), 4.54 (s, 2H), 4.40 (m, 2H), 4.06-4.11 (m, 3H), 4.00 (s, 3H), 3.92 (s, 3H), 3.61-3.63 (m, 3H), 2.98 (m, 2H), 2.67 (m, 1H), 2.54 (m, 1H), 2.32 (m, 2H), 2.15 (m, 2H), 1.98 (m, 2H), 1.84 (m, 2H), 1.45 (d, 3H, J=8.0 Hz), 1.09 (m, 3H).

MS (ESI negative mode): Calculated=1315.38; Observed=1315.34

Figure 13:
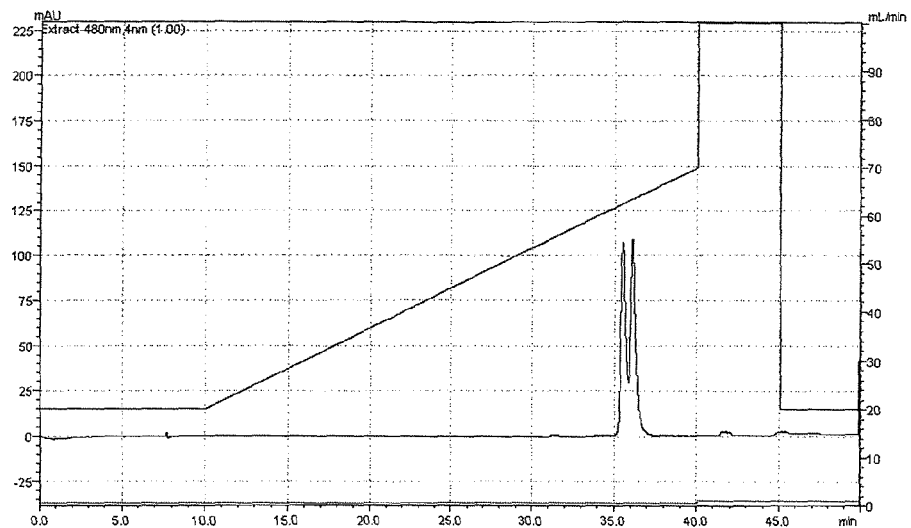
FIG. 13. RP-HPLC analysis of (3) at using detection at 480 nm. The two diastereomers have retention times of 35.8 and 36.9 min.

HPLC purity validation (see FIG. 13)

Photolytic Release of Doxorubicin from Drug Conjugate.

A solution (0.065 mM in 1 mL) of compound 6 in PBS was placed in a 60×15 mm well plastic dish placed on ice. The solution was irradiated and 70 μL was removed at various time points (0.5, 1, 2, 4, 8, 15, 20, and 30 minutes). Each assay was analyzed on RP-HPLC using isocratic elution of 20% organic eluent (0.1% TFA in acetonitrile) for 5 minutes and then using gradient elution from 20% to 70% for 30 minutes and was monitored at $\lambda_{abs}$=480 nm. (See FIG. 14).

Illumination Time-Dependant Toxicity.

JH-EsoAd1 cells were treated with media alone, media supplemented with EDANS (20 μM), or media supplemented with Dox-EDANS (9) (20 μM) in a 96 well clear-bottom, opaque plate. Cells were exposed to light (9 mW/cm$^2$) for various times (0-40 min) regulated by an aluminum foil mask. During the experiment the plate was kept in ice to reduce the heating by the UV lamp. After the lamp was turned off, the plate was covered with foil and placed at room temperature for an additional 80 min. The media was removed, and the cells were thoroughly washed with media (3×); then 200 μL of fresh media was added to each well. The plates were incubated for 72 hours at 37° C., following which the media was removed and 100 L of MTT (2 mg/ml) in phosphate buffered saline (PBS) was added to each well. After 3 hours, the MTT solution was removed and replaced with 100 μL of DMSO. The absorbance at 562 nm was analyzed via a plate reader.

Concentration Dependent Cell Viability Studies:

JH-EsoAd1 cells were treated with media supplemented with various concentrations of doxorubicin (0-6.4 μM) or Dox-EDANS (9) (0-16 μM) in a 96 well clear-bottom, opaque plate. Control wells were covered with aluminum foil while the remaining wells were exposed UV light (9 mW/cm$^2$) for 20 min. The plate was kept in ice during light exposure in order to minimize the heating. After irradiation, the plate was kept at it in the dark for another 100 minutes. The cells were washed and treated as above (time dependent toxicity experiments) to determine viability via the MTT assay.

Flow Cytometry Analysis of Permeability.

JH-EsoAd1 cells were seeded at 150,000 cells/well in 1.5 mL of media in 6 well plates. The cells were treated with media alone or media supplemented with 10 μM of EDANS-Dox (6). The plate was placed on ice, and the light treated cells were exposed to UV light (9 mW/cm$^2$) for 20 minutes. Following the light exposure the plates were kept at room temperature for 100 minutes. Then, the cells were washed with sterile PBS and trypsinized. For quantification of Dox fluorescence, treated cells were trypsinized, harvested, and washed with PBS at approximately 1×10$^6$ cells/mL. Pellets were fixed for 15 min at 37° C. with 3% paraformaldehyde in PBS. Samples were washed thoroughly with PBS, resuspended in PBS and analyzed by flow cytometry.

Confocal Microscopic Analysis of Permeability.

JH-EsoAd1 cells were seeded at 30,000 cells/well on 4 well glass chamber slides, and were treated as above (Flow cytometry analysis). The cells were treated with media alone or media supplemented with 10 μM of EDANS-Dox (6). The plate was placed on ice, and the light treated cells were exposed to UV light (9 mW/cm$^2$) for 20 minutes. Following the light exposure the plates were kept at room temperature for 100 minutes. The cells were washed extensively with PBS and fixed for 15 min at 37° C. with 3% paraformaldehyde in PBS. Slides were rinsed, dried and mounted under coverslips using Vectashield mounting media (Vector Laboratories, Inc.).

REFERENCES FOR EXAMPLE 1

1 F. Kratz, I. A. Muller, C. Ryppa and A. Warnecke, ChemMedChem, 2008, 3, 20-53.

2 F. Fischel-Ghodsian, L. Brown, E. Mathiowitz, D. Brandenburg and R. Langer, Proc. Natl. Acad. Sci. U.S.A., 1988, 85, 2403-2406.

3 G. M. Dubowchik, R. A. Firestone, L. Padilla, D. Willner, S. J. Hofstead, K. Mosure, J. O. Knipe, S. J. Lasch and P. A. Trail, Bioconjug. Chem., 2002, 13, 855-869.

4 M. Langer, F. Kratz, B. Rothen-Rutishauser, H. Wunderli-Allenspach and A. G. Beck-Sickinger, J. Med. Chem., 2001, 44, 1341-1348.

5 S. W. Choi, Y. Zhang and Y. Xia, Angew. Chem. Int. Ed Engl., 2010, 49, 7904-7908.

6 C. P. McCoy, C. Rooney, C. R. Edwards, D. S. Jones and S. P. Gorman, J. Am. Chem. Soc., 2007, 129, 9572-9573.

7 S. S. Agasti, A. Chompoosor, C. C. You, P. Ghosh, C. K. Kim and V. M. Rotello, J. Am. Chem. Soc., 2009, 131, 5728-5729.

8 S. K. Choi, T. Thomas, M. H. Li, A. Kotlyar, A. Desai and J. R. Baker Jr, Chem. Commun. (Camb), 2010, 46, 2632-2634.

9 O V. Gerasimov, J. A. Boomer, M. M. Qualls and D. H. Thompson, Adv. Drug Deliv. Rev., 1999, 38, 317-338.

10 H. M. Lee, D. R. Larson and D. S. Lawrence, ACS Chem. Biol., 2009, 4, 409-427.

11 A. Deiters, D. Groff, Y. Ryu, J. Xie and P. G. Schultz, Angew. Chem. Int. Ed Engl., 2006, 45, 2728-2731.
12 A. Deiters, ChemBioChem, 2010, 11, 47-53.
13 G. C. Ellis-Davies, Nat. Methods, 2007, 4, 619-628.
14 B. N. Goguen, B. D. Hoffman, J. R. Sellers, M. A. Schwartz and B. Imperiali, Angew. Chem. Int. Ed Engl., 2011, 50, 5667-5670.
15 C. W. Riggsbee and A. Deiters, Trends Biotechnol., 2010, 28, 468-475.
16 P. Agostinis, K. Berg, K. A. Cengel, T. H. Foster, A. W. Girotti, S. O. Gollnick, S. M. Hahn, M. R. Hamblin, A. Juzeniene, D. Kessel, M. Korbelik, J. Moan, P. Mroz, D. Nowis, J. Piette, B. C. Wilson and J. Golab, C A Cancer. J. Clin., 2011, 61, 250-281.
17 D. E. Dolmans, D. Fukumura and R. K. Jain, Nat. Rev. Cancer., 2003, 3, 380-387.
18 K. Berg, A. Weyergang, L. Prasmickaite, A. Bonsted, A. Hogset, M. T. Strand, E. Wagner and P. K. Selbo, Methods Mol. Biol., 2010, 635, 133-145.
19 K. Berg, M. Folini, L. Prasmickaite, P. K. Selbo, A. Bonsted, B. O. Engesaeter, N. Zaffaroni, A. Weyergang, A. Dietze, G. M. Maelandsmo, E. Wagner, O. J. Norum and A. Hogset, Curr. Pharm. Biotechnol., 2007, 8, 362-372.
20 M. Verhille, P. Couleaud, R. Vanderesse, D. Brault, M. Barberi-Heyob and C. Frochot, Curr. Med. Chem., 2010, 17, 3925-3943.
21 Note: Drug delivery via light-stimulated release of cytotoxins from cell impermeable polymers or nanoparticles has recently been described (e.g see refs 6-8). Our PCP approach is distinct because permeability is blocked by a cell impermeable small molecule.
22 T. Fichert, M. Yazdanian and J. R. Proudfoot, Bioorg. Med. Chem. Lett., 2003, 13, 719-722.
23 C. P. Holmes, J. Org. Chem., 1997, 62, 2370-2380.
24 G. Marriott, Biochemistry, 1994, 33, 9092-9097; R. Iwase, A. Kitani, T. Yamaoka and A. Murakami, Nucleic Acids Res. Suppl., 2003, (3), 61-62; L. Baumann and A. G. Beck-Sickinger, Biopolymers, 2010, 94, 771-778; L. Berrade, Y. Kwon and J. A. Camarero, Chembiochem, 2010, 11, 1368-1372; R. Yang, K. K. Pasunooti, F. Li, X. W. Liu and C. F. Liu, Chem. Commun. (Camb), 2010, 46, 7199-7201; J. P. Pellois, M. E. Hahn and T. W. Muir, J. Am. Chem. Soc., 2004, 126, 7170-7171; M. I. Sanchez, O. Vazquez, M. E. Vazquez and J. L. Mascarenas, Chem. Commun. (Camb), 2011, 47, 11107-11109; S. Cho, S. H. Lee, W. J. Chung, Y. K. Kim, Y. S. Lee and B. G. Kim, Electrophoresis, 2004, 25, 3730-3739; Z. Gu, A. Biswas, K. I. Joo, B. Hu, P. Wang and Y. Tang, Chem. Commun. (Camb), 2010, 46, 6467-6469; Y. Luo, N. V. Eldho, H. O, Sintim and T. K. Dayie, Nucleic Acids Res., 2011, 39, 8559-8571; J. B. Biggins, A. Hashimoto and J. T. Koh, Chembiochem, 2007, 8, 799-803; G. Mayer and A. Heckel, Angew. Chem. Int. Ed Engl., 2006, 45, 4900-4921.
25 A. Hector, J. M. Koorstra, S. Hong, J. J. Boonstra, W. N. Dinjens, A. A. Foratiere, T. Wu, E. A. Mongomery, J. R. Eshleman, A. Maitra, Cancer Biol. Ther. 2008, 7, 1753-1755.
26 G. Speelmans, R. W. Staffhorst, H. G. Steenbergen and B. de Kruijff, Biochim. Biophys. Acta, 1996, 1284, 240-246.

Example 2

Switchable Peptides as Agents for Cellular Delivery

Although peptides themselves are typically impermeable to cells, researchers have recently discovered a wide variety of cell-penetrating peptides, short peptide tags that are able to deliver otherwise impermeable molecules across cell membranes. There are several classes of peptides with this capability including tat, penetratin, and oligo-Arg sequences (e.g. see US patent application 20120100569 to Liu; David R.; et al, the complete contents of which is hereby incorporated by reference in entirety). What these sequences have in common is a large percentage of amino acids with positive charges, typically arginines, which are known to interact with sulfated carbohydrates on the cell surface as a part of the delivery process (e.g. see U.S. Pat. No. 7,173,130 to Tsien, et al and U.S. Pat. No. 8,258,256 to Denmeade, et al, the complete contents of each of which is hereby incorporated by reference in entirety).

Very recently, it has also been discovered that adding a patch of arginines to the surface of an impermeable protein makes it membrane permeable [1,2]. This technique has been termed arginine grafting. In an initial example, a cell permeable variant of GFP was created by mutating five surface residues in close proximity to arginine [1]. This approach has been also applied to a class of miniature proteins. In this case, certain residues on a single face of an alpha-helical region of the miniature protein were mutated to arginine [3]. As little as four arginines on the face of the helix afforded permeability, and miniproteins with 5-arginines on a single face were between 3-30 fold more cell permeable than classic cell penetrating peptides [3]. Since oligo-arginine peptides that contain fewer than six arginines are not typically cell permeable [4], the entry of these miniature proteins into cells is undoubtedly controlled by the display of the arginines in a single face of the helix, similar to an arginine graft.

This example describes the design of peptides existing either as a membrane permeable α-helix with four arginines on one face or as a membrane impermeable random coil with the arginines spatially dispersed. Conformational control between the two states is mediated by light, creating a method for light-controlled cellular delivery.

Photoswitchable Control of Peptide Conformation and Permeability

Figure 15:
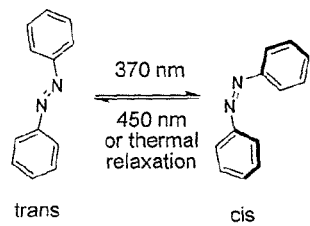
FIG. 15. Schematic representation of azobenzene photoswitching.

Azobenzene photoswitches have been developed as a method for controlling the conformation of molecules in the presence of light. Irradiation with light of the appropriate wavelength facilitates an extremely rapid (~1 ps) switch from the ground, dark adapted trans conformation, to the cis conformation with a quantum yield of 0.5. Such a conformational switch is shown in FIG. 15. Reversion of the cis to trans state can be facilitated with longer wavelength light (although some of the cis form still remains) or by thermal relaxation at ambient temperature leading completely to the trans state (in the ground state of free azobenzene, the cis form exists in less than 0.000001%). Depending on the substituents, in the dark the cis form of an azobenzene can have a half-life that varies from milliseconds to several hours. Both the half-life and the wavelengths used for photoswitching can be tuned dramatically through substitution of groups on the aromatic rings.

Figure 16:
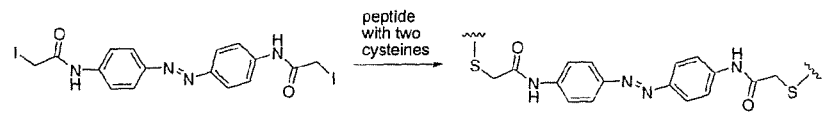
FIG. 16. Bis-alkylation of a peptide with an azobenzene molecule.
Figure 17:
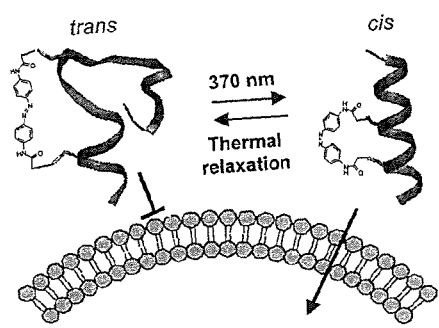
FIG. 17. Schematic representation of photoswitchable drug delivery.
Figure 18:
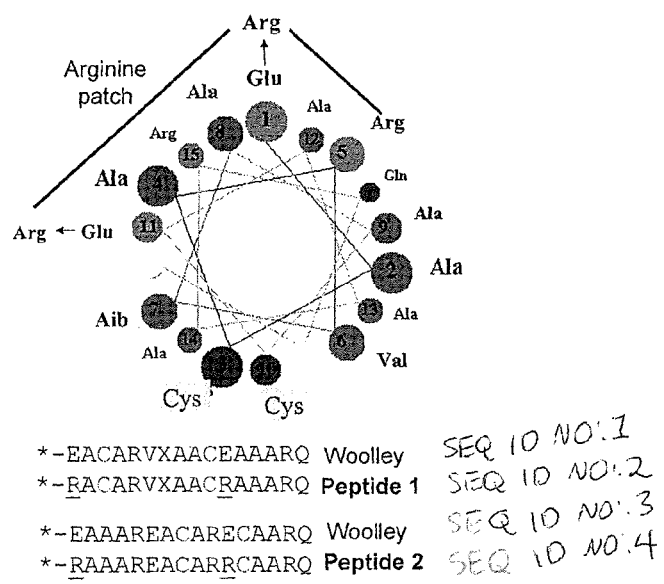
FIG. 18. Design of photoswitchable peptides with arginine patch. The linear and helical wheel depictions of the sequence are shown. The arginine patch is highlighted. A similar design strategy has been employed with peptide 2. The * refers to an attachment point for a drug, but is omitted in the helical wheel for clarity. X=2-aminoisobutyric acid.

Importantly, azobenzene photoswitches have been used to control the conformation of several different peptides with α-helical structure. Woolley and coworkers designed a crosslinking azobenzene with two iodoacetamide groups for attachment to a peptide containing two cysteines (FIG. 16). The resulting cyclic peptides underwent conformational changes as a result of conversion of the photoswitch from trans to cis and vice versa. Based on computations, they determined that the cis conformation of this photoswitch requires the two sulfur atoms to be between 6 and 14.6 Å apart. In the more rigid trans conformation, the favored distances are 17.1-18.7 Å apart. An alpha helix also puts distance constraints on the side chains of its amino acids. If these constraints are matched to the azobenzene's, the photoswitch will favor helix formation; if the constraints are incompatible, the photoswitch will destabilize a helix. Woolley has thus shown that it is possible to design a helix that is stabilized by one conformation of the azobenzene photoswitch and destabilized by another (FIG. 17). If cysteines within a potentially helical peptide are placed at the i, i+4, or i, i+7 positions, the cis form of the photoswitch but not the trans is compatible with a helix. In the i, i+11 positions, the trans form of the photoswitch is compatible, but not the cis. As such, one can create or destroy helicity within a peptide by choosing the positions for the photoswitch attachment.

Demonstration of Photoswitching by CD and HPLC.

CD spectra from the photoswitching of Peptide 1 in the presence of 370 nm light are shown in FIG. 19A. As expected, irradiation makes the peptide more α-helical as shown by a shift in the minimum at 200 nm to longer wavelength, and an increase in the minimum at 222 nm (FIG. 19A). After 30 minutes in the dark, the peptide had reverted mostly back to the more random coiled state.

We also monitored the switching of the azobenzene by HPLC, since we were able to separate both the cis and trans peptide isomers (FIG. 19B). After illumination the cis isomer reverted to the trans isomer over time. By fitting the areas under the peaks to an exponential decay equation we were able to estimate both the half-life and the percentage of cis isomer upon illumination, which were 47 min and 55% respectively. The half-life is in line with measurements of similar peptides, but the % cis is lower than the typical 80-95%. Use of a filter to eliminate the longer wavelength light (our light source has a spike of intensity at 405 nm which can promote cis to trans reversion) would enhance photoswitching upon irradiation.

These studies demonstrate our ability to prepare arginine-rich photoswitchable peptides that improve their α-helical propensity upon illumination.

REFERENCES FOR EXAMPLE 2

1. Fuchs, S. M.; Raines, R. T. Arginine grafting to endow cell permeability, ACS Chem Biol 2007, 2, 167-170.
2. McNaughton, B. R.; Cronican, J. J.; Thompson, D. B.; Liu, D. R. Mammalian cell penetration, siRNA transfection, and DNA transfection by supercharged proteins, Proc Natl Acad Sci USA 2009, 106, 6111-6116.3. Smith, B. A.; Daniels, D. S.; Coplin, A. E.; Jordan, G. E.; McGregor, L. M.; Schepartz, A. Minimally cationic cell-permeable miniature proteins via alpha-helical arginine display, J Am Chem Soc 2008, 130, 2948-2949.
4. Goun, E. A.; Pillow, T. H.; Jones, L. R.; Rothbard, J. B.; Wender, P. A. Molecular transporters: synthesis of oligoguanidinium transporters and their application to drug delivery and real-time imaging, Chembiochem 2006, 7, 1497-1515.

Example 3

Optimization of Peptide Properties for Use in the Practice of the Invention

Peptides are further designed, tested and tuned to optimize one or more of the following properties: membrane permeability (e.g. by adjusting the number of arginines in the peptide and/or their spacing); helicity (e.g. stabilizing the helix by N-terminal capping or substituting α-aminoisobutyric acid for alanine, or incorporating α-methylated cysteine; destabilizing the helix by substituting glycine for alanine); by changing the type and/or location of the switchable element; altering biostability by incorporating D amino acids; etc. Exemplary peptides are shown below:

```
                                       SEQ ID NO: 2
1. *CRACARVXAACRAAARQ

SEQ ID NO: 3
2. *CRAAAREACARRCAARQ

SEQ ID NO: 5
3. #RACARVXAACRAAARQ
```

In these exemplary peptides, X=2-aminoisobutyric acid

*=peptides in which the starred C-terminal cysteine is the site of drug attachment

=a peptide in which, in addition to the attachment of one or more drugs at cysteine residues, a small molecule (e.g. a detectable label such as 5-carboxyfluorescein) may be attached directly onto the N-terminus of the peptide Experiments have been conducted in which: the underlined cysteines have been reacted with bis-iodoacetamido-4,4'aminoazobenzene forming a cyclic structure (FIG. 16), in order to test photoswitching; and in which 5-carboxyfluorescein was attached to the N-terminus of SEQ ID NO: 5.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A conjugate for delivering a membrane permeable drug into cells, consisting of: said membrane permeable drug, and a membrane impermeable moiety chemically attached to said membrane permeable drug, wherein said membrane impermeable moiety comprises a peptide that adopts an α-helical conformation and becomes membrane permeable upon exposure to light.

2. The conjugate of claim 1, wherein said membrane impermeable moiety is chemically attached to said membrane permeable drug via a photolabile linkage.

3. The conjugate of claim 1, wherein said membrane permeable drug is doxorubicin.

4. The conjugate of claim 1 wherein said membrane permeable drug is selected from the group consisting of doxorubicin, epirubicin, *vinca* alkaloids, 5-fluorouracil, taxol, auristatins, maytansine, mertansine, tubulysins, camptothecin, didemnins, cisplatin, methotrexate, and calecheamycin.

5. The conjugate of claim 1 wherein said membrane permeable drug is selected from the group consisting of isotretinoin, tetracycline antiobiotics, trimethoprim, sulfamethoxazole, and azithromycin.

6. The conjugate of claim 1 wherein said membrane permeable drug is selected from the group consisting of Vitamin A derivatives, cyclosporin, hydroxyurea, thioguanine, and corticosteroids.

7. The conjugate of claim 1 wherein said membrane permeable drug is selected from the group consisting of 5-fluoro uracil and imiquimod.

8. The conjugate of claim 1 wherein said membrane impermeable moiety is selected from the group consisting of fluorescent sulfonated molecules, pyrene sulfonates, Alexa Fluor analogs, cyanine analogs, aryl or alkyl sulfonates, phosphates, phosphonates and carboxylic acids, carbohydrates, hydrophilic polymers, and hydrophilic nanoparticles.

9. The conjugate of claim 1 wherein said membrane impermeable moiety is a hydrophilic molecule or nanoparticle.

10. A conjugate for delivering a membrane permeable drug into cells, comprising: said membrane permeable drug, and a membrane impermeable moiety chemically attached to said membrane permeable drug, wherein said membrane impermeable moiety is a hydrophilic molecule or nanoparticle that adopts an α-helical conformation and becomes membrane permeable upon exposure to light.

* * * * *